United States Patent
Muniz et al.

(10) Patent No.: US 11,596,216 B2
(45) Date of Patent: Mar. 7, 2023

(54) HAIR TREATMENT COMPOSITIONS, SYSTEMS, DEVICES AND METHODS

(71) Applicant: WELLA INTERNATIONAL OPERATIONS SWITZERLAND SARL, Petit-Lancy (CH)

(72) Inventors: Dena Muniz, Mountain Lakes, NJ (US); Leobaldo Antonio Perdomo, Hackettstown, NJ (US); George Scott Kerr, Mason, OH (US); Aideen Noelle Ripley, Montclair, NJ (US); Chad Lafeldt, New York, NY (US); Jeffrey Miller, Morristown, NJ (US); Christina Bishop, Clifton, NJ (US); Carin Freidag, Norwalk, CT (US); William Demarest, Franklin Park, NJ (US)

(73) Assignee: WELLA INTERNATIONAL OPERATIONS SWITZERLAND SARL, Petit-Lancy (CH)

( * ) Notice: Subject to any disclaimer, the term of this patent is extended or adjusted under 35 U.S.C. 154(b) by 224 days.

(21) Appl. No.: 17/046,062

(22) PCT Filed: Apr. 9, 2019

(86) PCT No.: PCT/US2019/026526
§ 371 (c)(1),
(2) Date: Oct. 8, 2020

(87) PCT Pub. No.: WO2019/199779
PCT Pub. Date: Oct. 17, 2019

(65) Prior Publication Data
US 2021/0037944 A1 Feb. 11, 2021

Related U.S. Application Data

(60) Provisional application No. 62/656,879, filed on Apr. 12, 2018, provisional application No. 62/789,299, filed on Jan. 7, 2019.

(51) Int. Cl.
*A61Q 5/10* (2006.01)
*A45D 19/00* (2006.01)
(Continued)

(52) U.S. Cl.
CPC ....... *A45D 19/012* (2021.01); *A45D 19/0083* (2021.01); *A61K 8/062* (2013.01);
(Continued)

(58) Field of Classification Search
CPC .......... A61Q 5/10; A61Q 5/065; A61K 8/046; A61K 2800/43; A61K 2800/4322;
(Continued)

(56) References Cited

U.S. PATENT DOCUMENTS

2004/0068805 A1 4/2004 Fishman
2008/0083420 A1* 4/2008 Glenn .................... A61Q 5/065
132/270
(Continued)

FOREIGN PATENT DOCUMENTS

EP 2291172 B1 10/2017
JP 2001122364 A 5/2001
WO WO-2019199779 A1 10/2019

OTHER PUBLICATIONS

"International Application Serial No. PCT/US2019/026526, International Search Report dated Sep. 18, 2019", 7 pgs.
(Continued)

*Primary Examiner* — Eisa B Elhilo
(74) *Attorney, Agent, or Firm* — Dennemeyer & Associates LLC; Victoria Friedman

(57) ABSTRACT

A hair treatment kit comprises a hair treatment composition selected from the group of semi-permanent oxidative and/or direct dye hair colorant compositions, hair bleaching compositions, highlighting compositions, and combinations thereof, a reservoir for holding the temporary hair treatment
(Continued)

composition, and an applicator fluidly connected to the reservoir for selectively applying the hair treatment composition to a targeted area of hair. Methods of applying the hair treatment composition comprise selectively engaging the applicator with a targeted area of hair, leaving the hair treatment composition in the targeted area for a time period, washing the hair treatment composition out of the targeted area, closing the reservoir to preserve remaining hair treatment composition for later use, and reapplying the hair treatment composition to the targeted area.

18 Claims, 8 Drawing Sheets

(51) Int. Cl.
    *A61K 8/06*     (2006.01)
    *A61Q 5/06*     (2006.01)
    *A61Q 5/08*     (2006.01)

(52) U.S. Cl.
    CPC ............... *A61Q 5/065* (2013.01); *A61Q 5/08* (2013.01); *A61Q 5/10* (2013.01); *A45D 19/0066* (2021.01); *A45D 2200/051* (2013.01); *A45D 2200/058* (2013.01); *A45D 2200/25* (2013.01); *A61K 2800/432* (2013.01); *A61K 2800/87* (2013.01)

(58) Field of Classification Search
    CPC .......... A61K 2800/432; A61K 2800/87; A45D 19/0083; A45D 19/0066; A45D 2200/051; A45D 2200/058
    USPC ........................................................ 132/208
    See application file for complete search history.

(56) References Cited

U.S. PATENT DOCUMENTS

| | | | |
|---|---|---|---|
| 2008/0087293 A1* | 4/2008 | Glenn | A45D 19/024 424/70.2 |
| 2015/0053228 A1* | 2/2015 | Bonauer | A45D 19/012 132/208 |
| 2015/0053229 A1* | 2/2015 | Bonauer | A61K 8/22 132/286 |
| 2015/0053232 A1* | 2/2015 | Schofield | A45D 19/0083 132/208 |

OTHER PUBLICATIONS

"International Application Serial No. PCT/US2019/026526, Invitation to Pay Additional Fees dated Jul. 23, 2019", 12 pgs.
"International Application Serial No. PCT/US2019/026526, Written Opinion dated Sep. 18, 2019", 12 pgs.
"Ultimate Colour Regrowth Application", Schwartzkopf Australia, Youtube, (Jun. 5, 2013), 1 pg.

* cited by examiner

HAIR TREATMENT COMPOSITIONS, SYSTEMS, DEVICES AND METHODS

CLAIM OF PRIORITY

This patent application is a U.S. National Stage Filing under 35 U.S.C. 371 from International Application No. PCT/US2019/026526, filed on Apr. 9, 2019, and published as WO 2019/199779 on Oct. 17, 2019, which application claims the benefit of priority to U.S. Application Ser. No. 62/789,299, filed Jan. 7, 2019, as well as U.S. Application Ser. No. 62/656,879, filed Apr. 12, 2018, which are incorporated by reference herein in their entirety.

TECHNICAL FIELD

This document pertains generally, but not by way of limitation, to systems and methods for treating hair. More specifically, but not by way of limitation, the present application relates to combinations of compositions of dyes with applicators for applying such dyes.

BACKGROUND

Dyes are used to change the color of hair. Sometimes it is not desirable to apply the dye to every hair on the scalp. Dyes can be applied with applicators comprising of bottles or tubes that dispense a liquid dye to the hair. However, dyes are not always permanent and can wash-out or lose their effectiveness over time. As such, it can be desirable to reapply the dye, thus requiring the consumer to reacquire or repurchase a dye and a dye applicator.

OVERVIEW

The present inventors have recognized, among other things, that a problem to be solved can include the difficulty of applying hair dye to only certain portions or sections of hair on a scalp. Furthermore, it can be difficult to preserve dye contained in applicators for future applications. With permanent hair colorants, once mixed/activated, it is not possible to store and re-use.

The present subject matter can help provide solutions to these problems, such as by providing a hair dye composition in a hair dye applicator that can be configured to apply the dye only certain portions or sections of hair of a scalp and that can be sealed in an air-tight manner to preserve the remaining dye for future applications.

In a particular example, an applicator assembly or device can include a collapsible body or tube that can contain an oxidative or direct dye treatment composition agent that can be dispensed through an applicator head coupled to the collapsible body or tube via an interface that can withstand repeated exposure to the hair treatment compositions and that can close-up to prevent air from being drawn back into the collapsible body or tube.

In an example, a method for treating hair strands with a treatment composition contained in an applicator device comprises grasping an applicator device having a reservoir containing a temporary hair treatment composition comprised of a semi-permanent oxidative and/or direct dye hair color, applying pressure to the applicator device to force the temporary hair treatment composition out of a nozzle of the applicator device, flowing the temporary hair treatment composition from the nozzle into an applicator assembly attached to the nozzle, engaging the applicator assembly directly with a target area of the hair strands, leaving the temporary hair treatment on the target area for a time period, rinsing the temporary hair treatment composition from the strands, and closing the applicator device to preserver any temporary hair treatment composition remaining in the reservoir.

In another example, a hair treatment kit comprises a hair treatment composition selected from the group of semi-permanent oxidative or direct dye hair colorant compositions, hair bleaching compositions, highlighting compositions, and combinations thereof, a reservoir for holding the temporary hair treatment composition, and an applicator fluidly connected to the reservoir for selectively applying the hair treatment composition to a targeted area of hair.

In an additional example, an applicator device for applying a semi-permanent oxidative or direct dye hair colorant composition to a selected area of hair comprises a collapsible body defining a reservoir for holding the hair colorant composition, a body head connected to the collapsible body and defining a nozzle in fluid communication with the reservoir, an applicator assembly connected to the body head comprising a valve body configured to engage the nozzle to selectively permit flow from the reservoir, an applicator mechanically attached to the valve body to receive flow from the valve body, and a holder having an opening through which a portion of the applicator can extend, the holder coupled to the body head, and a spring located between the body head and the valve body to bias the applicator assembly away from the body head.

This overview is intended to provide an overview of subject matter of the present patent application. It is not intended to provide an exclusive or exhaustive explanation of the invention. The detailed description is included to provide further information about the present patent application.

Figure 1:
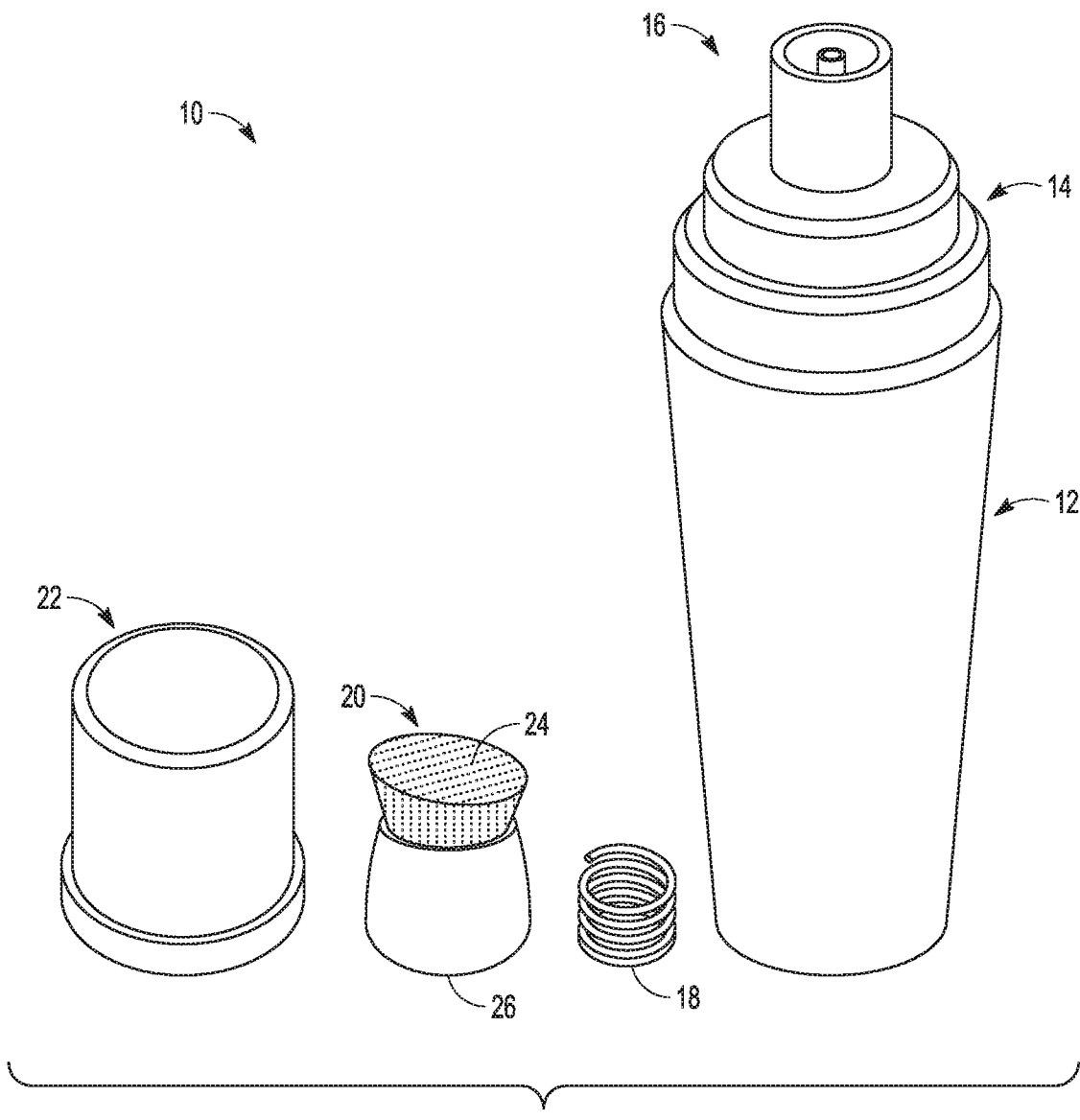
FIG. 1 is a partially exploded view of a hair dye applicator of the present application showing a tube having a tube head with a nozzle, a spring, a brush assembly and a cap.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 is a partially exploded view of hair dye applicator device 10 of the present application showing tube 12 having tube head 14 with nozzle 16, spring 18, brush assembly 20 and cap 22.

Hair dye applicator device 10 can be configured for dispensing or applying a liquid hair dye, such as an oxidative or direct dye composition, or some other hair treatment composition. Compositions other than liquids can be dispensed or applied. Tube 12 can be configured to hold a volume of liquid hair dye and, when compressed or otherwise subjected to pressure, force or push said liquid hair dye through tube head 14 and into nozzle 16. Tube 12 can be fabricated from a material that can be deformed and hold its shape. Spring 18 can be positioned between tube head 14 and brush assembly 20 to bias brush assembly 20 away from nozzle 16, thereby opening nozzle 16. Cap 22 can be configured to be positioned over brush 24 of brush assembly 20 to push down on brush holder 26 to close nozzle 16. As such, exposure of the liquid hair dye within tube 12 to oxygen can be limited by a plurality of factors, such as the ability of tube 12 to hold its shape in a collapsed condition, thereby preventing oxygen from being drawn back into tube 12, the ability of cap 22 to prevent air from entering nozzle 16, and the engagement of components of brush assembly 20, such as brush valve 28 (FIG. 3), with nozzle 16 to close-off nozzle 16.

However, with cap 22 removed, spring 18 can push brush assembly 20 away from nozzle 16 to connect the interior of tube 12 with brush 24 via nozzle 16. As such, tube 12 can be compressed to force liquid hair dye through nozzle 16 and into brush 24. As such, brush 24 can be drawn through hair follicles to selectively apply the liquid hair dye to portions hair of a scalp.

Figure 2:
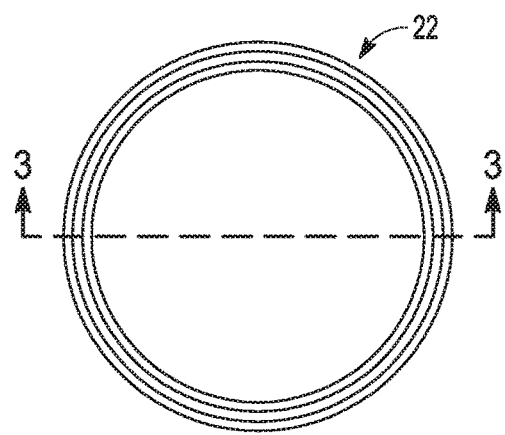
FIG. 2 is a top view of the hair dye applicator of FIG. 1 with the cap assembled onto the tube head to enclose the spring and the brush assembly.
Figure 3:
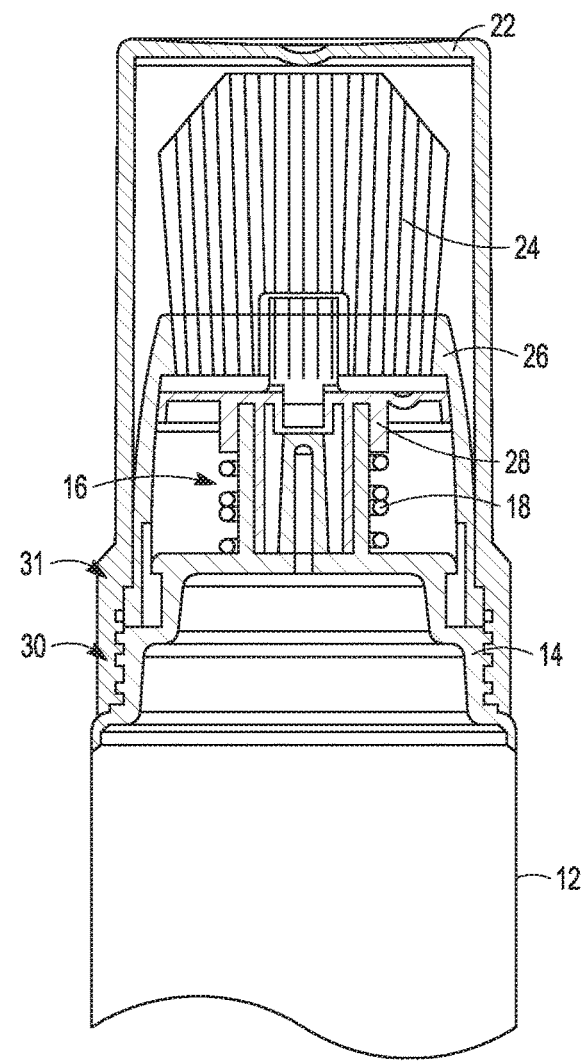
FIG. 3 is a side cross-sectional view of the hair dye applicator of FIG. 2 taken at section 3-3 to show the spring positioned between the nozzle and the brush assembly.

FIG. 2 is a top view of hair dye applicator device 10 of FIG. 1 with cap 22 assembled onto tube head 14 to enclose spring 18 and brush assembly 20. FIG. 3 is a side cross-sectional view of hair dye applicator device 10 taken at section 3-3 of FIG. 2 to show spring 18 positioned between nozzle 16 and brush assembly 20. FIGS. 2 and 3 are discussed concurrently.

Brush assembly 20 can comprise brush 24, brush holder 26 and brush valve 28. Cap 22 can engage tube head 14 at threaded connection 30. When threaded connection 28 is fully engaged, cap 22 can push brush holder 28 toward tube 12 at interface 31. As such, brush valve 28 can be pushed against nozzle 16 to close-off or inhibit flow of liquid hair dye from nozzle 16. When cap 22 is removed, brush valve 28 is pushed away from tube head 14 via spring 18, thereby opening nozzle 16.

Hair dye applicator device 10 can prevent exposure of liquid hair dye within tube 12 to atmospheric conditions, such as oxygen present in the air, via three mechanisms. First, tube 12 can be configured to deform and hold its shape such that when liquid hair dye is pushed out of tube 12, tube 12 does not expand or return to its previous, undeformed shape to prevent air from being drawn backwards into tube 12 through nozzle 16. Tube 12 can therefore be fabricated from suitable materials that can be semi-permanently deformed and that prevent transmission of air therethrough, as described below. Second, closure of nozzle 16 via engagement with brush valve 28 prevents air from entering tube 12. As such, nozzle 16 and brush valve 28 can be configured as a valve stem and valve seat to inhibit egress of liquid hair dye and ingress of air, as described below. Third, cap 22 provides a seal or barrier around the outside of nozzle 16 to additionally prevent air from entering tube 12. As such, cap 22 can be provided with a threaded engagement with tube head 14 to push brush holder 26 down to engage brush valve 28 with nozzle 16 in a firm manner and to tightly seal between tube head 14 and cap 22.

Configurations and operation of the components of hair dye applicator device 10 are discussed with reference to FIGS. 4-19.

Figure 6:
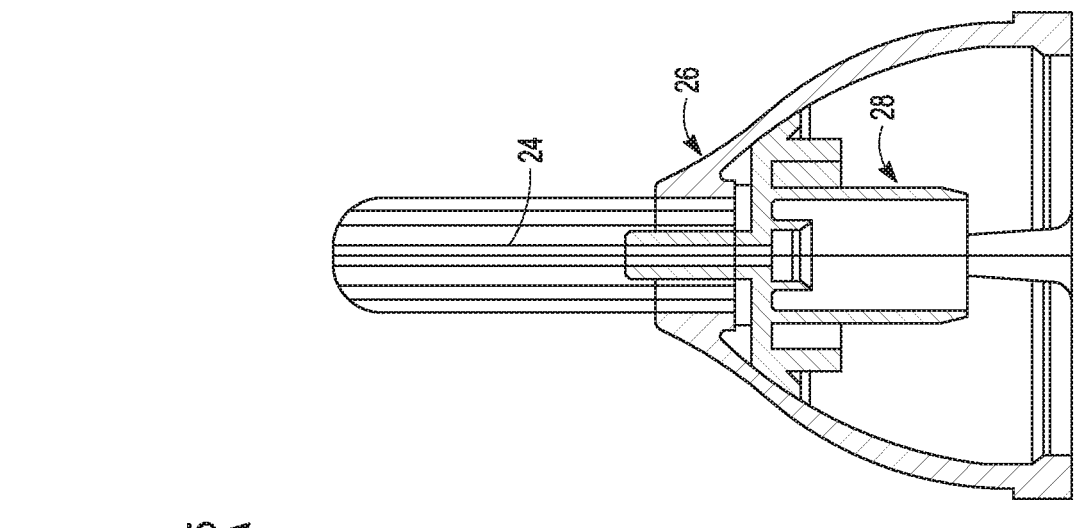
FIG. 6 is a cross-sectional view of the brush assembly taken at section 6-6 of FIG. 4 to show a thickness of the brush captured between the brush valve and the brush holder.
Figure 4:
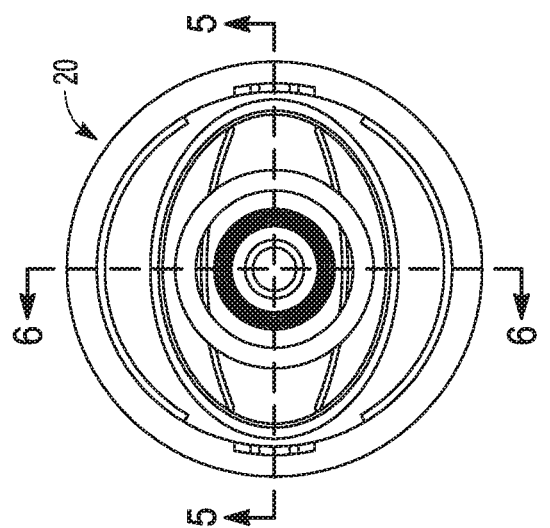
FIG. 4 is a bottom view of the brush assembly of FIG. 1 showing a brush holder and a brush valve.
Figure 5:
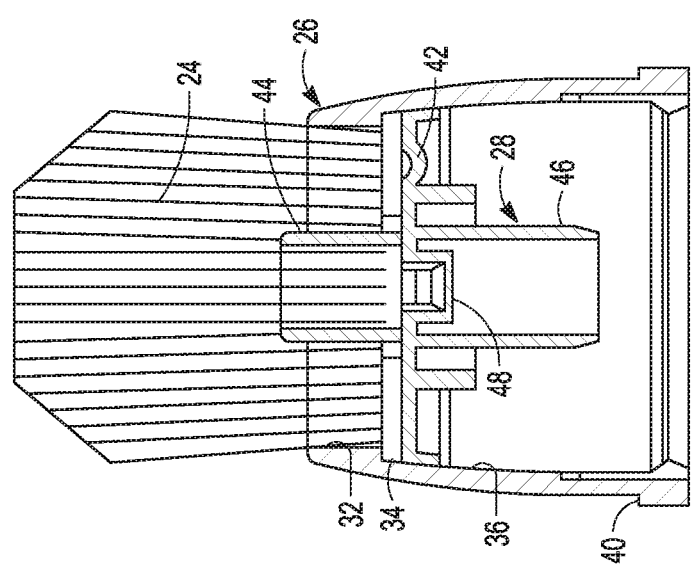
FIG. 5 is a cross-sectional view of the brush assembly taken at section 5-5 of FIG. 4 to show a width of a brush captured between the brush valve and the brush holder.

FIG. 4 is a bottom view of brush assembly 20 of FIG. 1 showing brush holder 26 and brush valve 28. FIG. 5 is a cross-sectional view of brush assembly 20 taken at section 5-5 of FIG. 4 to show brush 24 captured between brush valve 28 and brush holder 26. FIG. 6 is a cross-sectional view of brush assembly 20 taken at section 6-6 of FIG. 4 to show brush 24 captured between brush valve 28 and brush holder 26. FIGS. 4-6 are discussed concurrently. Brush holder 26 can comprise brush socket 32, brush ledge 34, chamber 36, flange 38 and cap ledge 40. Brush valve 28 can comprise can comprise base 42, discharge stem 44, slide post 46 and valve seat 48.

Figure 9:
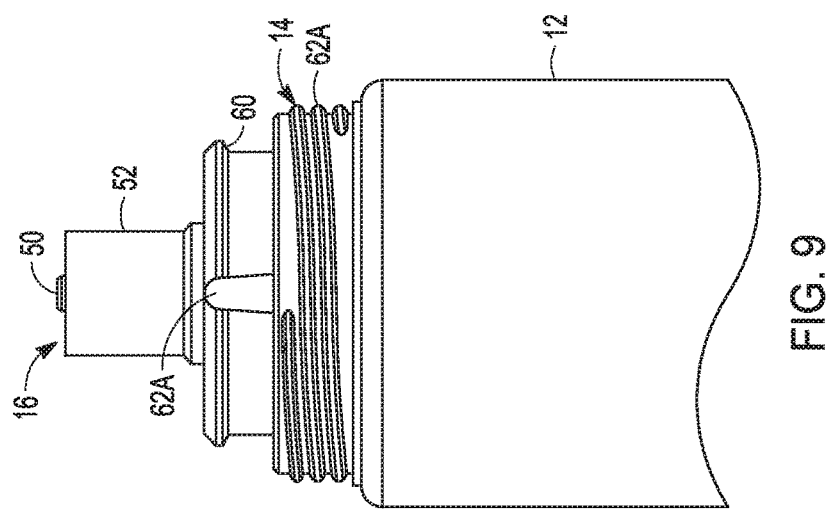
FIG. 9 is a side view of the tube of FIG. 7 showing threading for receiving the cap of FIGS. 10 and 11.
Figure 7:
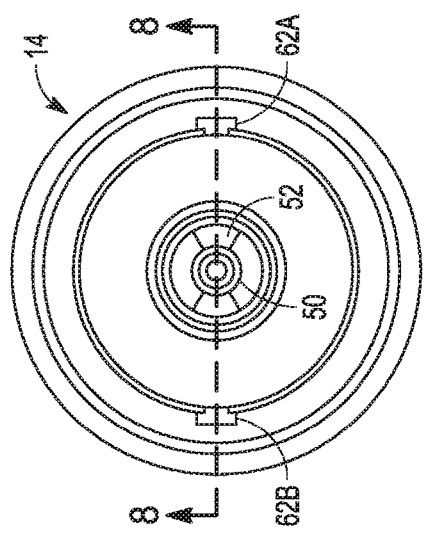
FIG. 7 is a top view of the tube head of FIG. 1 showing a baffle located inside the nozzle.
Figure 8:
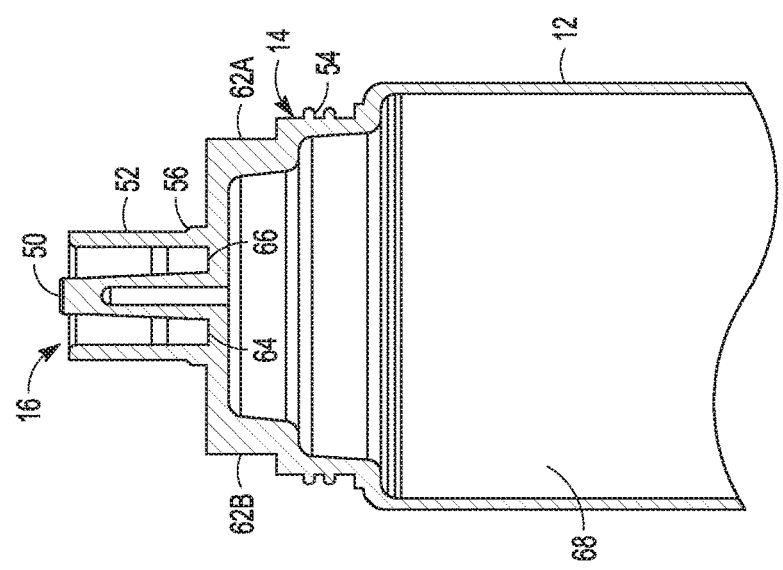
FIG. 8 is a cross-sectional view of the tube head taken at section 8-8 of FIG. 7 to show the baffle projecting into the nozzle.

FIG. 7 is a top view of tube head 14 of FIG. 1 showing baffle 50 located inside nozzle body 52 of nozzle 16. FIG. 8 is a cross-sectional view of tube head 14 taken at section 8-8 of FIG. 7 to show baffle 50 projecting into nozzle body 52. FIG. 9 is a side view of tube 12 of FIG. 7 showing threading 54 for receiving cap 22 of FIGS. 10 and 11. FIGS. 7-9 are discussed concurrently. Tube head 14 can further comprise spring shoulder 56, holder ledge 58, holder flange 60, holder rails 62A and 62B, one or more apertures 64 and one or more spokes 66. Tube 12 can comprise interior 68.

Tube 12 can be made of material sufficiently strong for holding hair compositions, preventing air from permeating through tube 12 and entering interior 68, and permitting tube 12 to be deformed and hold a collapsed shape. In an example, tube head 14 can be made of High Density PolyEthylene.

In examples, tube 12 can be made of plastics, such as cosmetic-grade plastics. Tube 12 and tube head 14 can be made of the same plastics or material, or of different materials.

In an example, tube 12 can comprise a glossy ABL (Aluminum Barrier Layer) laminate with a thickness of 0.275 mm and cap 22 can be made of PolyPropylene. Tube 12 may be made of plastics selected from the group consisting of polyethylene terephthalate (PET), polyethylene (PE), high density polyethylene (HDPE), low density polyethylene (LDPE), polyvinyl chloride (PVC), polyvinylidene chloride (PVDC), polypropylene (PP), polystyrene (PS), high-impact polystyrene (HLPS), polyamides (PA) (Nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), polyurethanes (PU), acrylonitrile butadiene styrene (ABS), Celluloid, Cellulose acetate, ethylene-vinyl acetate (EVA), ethylene vinyl alcohol (EVAL), liquid crystal polymer (LCP), polyacetal (POM or Acetal), polyacrylates (Acrylic), polyacrylonitrile (PAN or Acrylonitrile), polyamideimide (PAI), polyaryletherketone (PAEK or Ketone), polybutadiene (PBD), polybutylene (PB), polybutylene terephthalate (PBT), polycyclohexylene dimethylene terephthalate (PCT), polyhydroxyalkanoates (PHAs), polyketone (PK), polyester, polyethylene (PE) including low density (LDPE) and high density (HDPE) versions, polyetheretherketone (PEEK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), polysulfone (PSU), and mixtures thereof. Tube 12 can alternatively be made of plastics selected from polyolefines; alternatively, from the group consisting of high-density polyethylene (HDPE), low density polyethylene (LDPE), polypropylene (PP), polyethylene terephthalate (PET), derivatives thereof, and mixtures thereof; alternatively, from plastics being high-density polyethylene (HDPE). Commercially available HDPE are provided by Exxon under the trade name AS55-003. In an embodiment, tube 12 is made of high-density polyethylene and is substantially free of polyethylene tetraphthalate. In at least one embodiment, the container 1 comprises at least about 80%, or at least about 85%, or at least about 90%, or at least about 95% polyethylene.

In examples, tube 12 can be made of aluminum-based tubes, such as aluminum, tin/copper alloy, lead (any ductile metal that can be worked cold), polyolefin lined (polyethylene—PE, polypropylene—PP), and internally lined with wax, phenolics, epoxies, latex. In examples, tube 12 can be made of laminate tubes, such as polyethylene (HDPE, LDPE, LLDPE), polypropylene, ethyl vinyl alcohol, aluminum, and metalized foil. In examples, tube 12 can be made of extruded tubes or injection molded tubes, such as polyethylene (LDPE, HDPE, LLDPE), polypropylene, lacquer, varnish, and PET.

Aluminum-based tubes can comprise a collapsible metal container with an internal volume/reservoir manufactured from pigs and cast into slabs preparatory to rolling in to sheets, tumbled, lubricated, and sent to an extrusion press with a shallow female die and a male die shaped like the inside of the tube. The die closes on tube with considerable pressure and metal is squeezed out between the two parts, hugging the inner die as it moves rapidly around it. When the die separates, the tube is blown off with compressed air. Subsequent operations include cutting the thread, reaming the orifice, trimming to length, decorating and lining. May include flexible film or film laminate liners that may extend through to the neck and finish area. Orifices can include blind opening, screw-eye, and integral or separate application systems. Seamless body and or welded seam.

Laminate tubes can be constructed from multi-layer cast extruded polyethylene sheeting, (polyolefin, foil, polyolefin). They can be fed through forming rolls to form the tube body, sonic welding, heat seal. Heading includes preformed, injection, compression, usually through heat).

Extruded tubes can comprise molten polyolefins formed through extrusion (seamless), monolayer, dual layer, dual color, co-extrusion.

Injection molded tubes can comprise injection molding of plastic tube shape and extrusion blow molded tubes.

In additional examples, a reservoir for the hair treatment device can comprise a bottle or tottle made from Polyethylene terephthalate (PET), Polyethylene (PE), High-density polyethylene (HDPE), Polyvinyl chloride (PVC), Polyvinylidene chloride (PVDC) (Saran), Low-density polyethylene (LDPE), Polypropylene (PP), Polystyrene (PS), High impact polystyrene (HIPS), Polyamides (PA) (Nylons), Acrylonitrile butadiene styrene (ABS), Polyethylene/Acrylonitrile Butadiene Styrene (PE/ABS), Polycarbonate (PC), Polycarbonate/Acrylonitrile Butadiene Styrene (PC/ABS), Polyurethanes (PU), Acrylonitrile butadiene styrene (ABS), Acrylic, Celluloid, Cellulose acetate, Ethylene-Vinyl Acetate (EVA), Ethylene vinyl alcohol (EVAL), Fluoroplastics (PTFEs, including FEP, PFA, CTFE, ECTFE, ETFE), Ionomers, Kydex, a trademarked acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA or Nylon), Polyamide-imide (PAI), Polyaryletherketone (PAEK or Ketone), Polybutadiene (PBD), Polybutylene (PB), Polybutylene terephthalate (PBT), Polyethylene terephthalate (PET), Polycyclohexylene dimethylene terephthalate (PCT), Polycarbonate (PC), Polyhydroxyalkanoates (PHAs), Polyketone (PK), Polyester, Polyethylene (PE) including low density (LDPE) and high density (HDPE) versions, Polyetheretherketone (PEEK), Polyetherimide (PEI), Polyethersulfone (PES)—see Polysulfone, Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polypropylene (PP), Polystyrene (PS), Polysulfone (PSU), Polyvinyl chloride (PVC), Polyvinylidene chloride (PVDC), Spectralon. Most preferred are polyolefins, and in particular polyethylene, polyethylene terephthalate, polypropylene, or mixtures thereof. Any of the aforesaid may comprise bio derived (in part or whole) polymers or monomers that are then subject to polymerization. Such reservoirs can be made via various manufacturing processes as blow molding, compaction plus sintering, compression molding, expandable bead molding, extrusion blow molding, foam molding, injection molding, injection/stretch blow molding, laminating, reaction injection molding, matched mold, matrix molding, plastic molding, pressure plug assist molding, rotational molding (or Roto-molding), transfer molding, thermoforming, vacuum forming, and vacuum plug assist molding.

In additional examples, a reservoir for the hair treatment device can comprise a can made from aluminum, steel, tinplate steel via processes including aluminum disc/impact extrusion process; and welded, rimmed 2 and 3 piece can construction, 2-piece constructions comprising cup blanking and Drawing, Ironing and Doming, Trimming Cleaning, printing and varnishing, bottom vanishing, baking, inside spraying, baking, necking in, flanging/curling, 3-piece construction comprising large coil shearing, coating, printing, scroll shearing, end forming, body forming, flanging, spray coating, and baking.

In additional examples, a reservoir for the hair treatment device can comprise a sachet comprising a container or packet/pouch with internal volume/reservoir manufactured from flexible film or film laminate material and may include spout for dispensing product, and may include various opening features, i.e., perforations, notches, scores, tear strips, tear tabs, and may include one or more pieces of flexible film or film laminates. Sachets can be made from Extruded, blown, cast thermoplastic films and or combinations/laminates including metalized films, and Al films, and may be made by form/fill/seal methods, such as reel or reels of flexible material formed into container, filled, and sealed in single series of operations, a roll of material formed into a tube then filled and sealed, or a roll of material folded along length and sealed at intervals to form sachets which are filled and sealed at intervals. Equipment can be either horizontal or vertical machines.

Interior 68 can form a reservoir. This reservoir can comprise a total volume of from about 20 ml to about 1500 ml, alternatively from about 50 ml to about 1000 ml, alternatively from about 75 ml to about 500 ml, alternatively from about 100 ml to about 250 ml, alternatively from about 160 ml to about 170 ml, alternatively from about 15 ml to about 75 ml.

In examples, tube 12 can be substituted for a bottle, pouch, sachet, tottle or an airless canister. In other examples, tube 12 can be positioned within a bottle or a rigid structure.

A product, such as a hair dye liquid or hair dye composition (gel, milk, crème, foam or any other form that is suitable for lightening or dyeing keratin fibers) can be located in interior 68. In examples, oxidative and/or direct dye hair colors can be used. In examples, the product can comprise a beauty care component. The product can comprise a hair coloring and/or bleaching component comprising an oxidative agent, a direct dye, a fatty substance, an alkalizing agent, an oxidizing agent, a surfactant or mixtures thereof (further including other components used in the art for hair coloring and bleaching compositions). The component can comprise a source of an oxidizing agent. Any oxidizing agent known in the art may be used. Suitable oxidizing agents are water-soluble peroxygen oxidizing agents. As used herein, "water-soluble" means that in standard conditions at least about 0.1 g, alternatively about 1 g, alternatively about 10 g of the oxidizing agent can be dissolved in 1 litre of deionized water at 25° C. The component may comprise a total amount of oxidizing agent ranging from about 3% to about 12%, by weight of the total component. Suitable water-soluble oxidizing agents include but are not limited to: inorganic peroxygen materials capable of yielding hydrogen peroxide in an aqueous solution, alternatively, hydrogen peroxide, inorganic alkali metal peroxides, organic peroxides, inorganic perhydrate salt bleaching compounds, and mixtures thereof; alternatively, hydrogen peroxide, percarbonates, persulphates, and mixtures thereof. In at least one embodiment, the beauty care component comprises hydrogen peroxide ($H_2O_2$). The beauty care component may be a developer composition. The developer composition may be based on any desired formulation chassis, including any commercial product, for example an oil-in-water emulsion. In at least one embodiment, the developer composition comprises from about 6% to about 9% $H_2O_2$ relative to the total weight of the developer composition. In at least one embodiment, the component is a hair coloring and/or hair bleaching component comprising a total amount of oxidizing agent ranging from about 3% to about 12%, by weight of the total component. A commercial example is the Welloxon® Emulsion with respectively about 6% and about 9% $H_2O_2$, marketed by Wella and comprising as INCI ingredients: Water, $H_2O_2$, Cetearyl Alcohol, Ceteareth-25, Salicylic Acid, Phosphoric Acid, Disodium Phosphate, Etidronic Acid.

Fatty Substances

According to the invention, the dyeing or lightening composition can comprise at least 20% by weight of fatty substances free of carboxylic acid groups relative to the total weight of the composition.

The term "fatty substance" means an organic compound that is an insoluble organic in water at room temperature (25° C.) and at atmospheric pressure (760 mmHg) (solubility of less than 5%, such as 1% or 0.1%). In addition, under the same temperature and pressure conditions, the fatty substances are soluble in organic solvents such as chloroform, ethanol or benzene, for example.

The term "fatty substance free of carboxylic acid groups" means fatty substance containing no —COOH groups and no —COO groups.

In some embodiments, the fatty substances of the invention are selected from the group consisting of liquid hydrocarbons, non-silicone oils of animal, plant, mineral or synthetic origin, liquid fatty alcohols, liquid fatty esters, silicones and fatty ethers, or mixtures thereof.

The fatty substances of the invention may be liquid or non-liquid at room temperature (25° C.) and at atmospheric pressure (760 mmHg; i.e. $1.013 \times 10^5$ Pa). The liquid fatty substances of the invention preferably have a viscosity of less than or equal to 2 Pa·s, better less than or equal to 1 Pa·s and even better less than or equal to 0.1 Pa·s at a temperature of 25° C. and at a shear rate of 1 $s^{-1}$. The term "liquid hydrocarbon" means a hydrocarbon composed solely of carbon and hydrogen atoms, which is liquid at ordinary temperature (25° C.) and at atmospheric pressure (760 mmHg; i.e. $1.013 \times 10^5$ Pa).

More particularly, the liquid hydrocarbons are chosen from:
  linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane.
  linear or branched hydrocarbons of mineral, animal or synthetic origin with more than 16 carbon atoms, such as volatile or non-volatile liquid paraffins and derivatives thereof, petroleum jelly, liquid petroleum jelly, polydecenes, hydrogenated polyisobutene such as Parleam®, and squalane.

In some aspects, the liquid hydrocarbon(s) is (are) chosen from volatile or non-volatile liquid paraffins, and liquid petroleum jelly. In some aspects, the liquid hydrocarbon is liquid petroleum jelly.

The term "liquid fatty alcohol" means a non-glycerolated and non-oxyalkylenated fatty alcohol that is liquid at room temperature (25° C.) and at atmospheric pressure (760 mmHg; i.e. $1.013 \times 10^5$ Pa).

In some embodiments, the liquid fatty alcohols of the invention comprise from 8 to 30 carbon atoms.

The liquid fatty alcohols of the invention may be saturated or unsaturated. The saturated liquid fatty alcohols are preferably branched. They may optionally comprise in their structure at least one aromatic or non-aromatic ring. In some aspects they are acyclic.

More particularly, the liquid saturated fatty alcohols of the invention are chosen from octyldodecanol, isostearyl alcohol, 2-hexyldecanol and mixtures thereof. In some embodiments, the liquid saturated fatty alcohol of the invention is octyldodecanol.

These liquid unsaturated fatty alcohols have at least one double or triple bond. In some embodiments, the fatty alcohols of the invention bear in their structure one or more double bonds. When several double bonds are present, there are usually 2 or 3 of them, and they may be conjugated or non-conjugated. These unsaturated fatty alcohols may be linear or branched. They may optionally comprise in their structure at least one aromatic or non-aromatic ring. In some embodiments they are acyclic.

More particularly, the liquid unsaturated fatty alcohols of the invention are chosen from oleyl alcohol, linoleyl alcohol, linolenyl alcohol, undecylenyl alcohol and mixtures thereof.

The term "liquid fatty ester" means an ester derived from a fatty acid and/or from a fatty alcohol and that is liquid at room temperature (25° C.) and at atmospheric pressure (760 mmHg; i.e. $1.013 \times 10^5$ Pa).

The esters can be liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

In some aspects, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention is made of: diethyl sebacate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

Composition according to the invention may also comprise, as liquid fatty ester, sugar esters and diesters of $C_6$-$C_{30}$ and preferably $C_{12}$-$C_{22}$ fatty acids. The term "sugar" means oxygen-bearing hydrocarbon-based compounds which contain several alcohol functions, with or without aldehyde or ketone functions, and which comprise at least 4 carbon atoms. These sugars may be monosaccharides, oligosaccharides or polysaccharides.

Examples of suitable sugars include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

Monoesters and diesters and especially sucrose, glucose or methylglucose monooleates or dioleates, stearates, behenates, oleopalmitates, linoleates, linolenates and oleostearates are more particularly used.

Finally, natural or synthetic esters of monoacids, diacids or triacids with glycerol may also be used.

Among these are plant oils. As oils of plant origin or synthetic triglycerides that may be used in the composition of the invention as liquid fatty esters, examples include:

triglyceride oils of plant or synthetic origin, such as liquid fatty acid triglycerides comprising from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, jojoba oil and shea butter oil.

The term "liquid silicone" means an organopolysiloxane that is liquid at room temperature (25° C.) and at atmospheric pressure (760 mmHg; i.e. $1.013 \times 10^5$ Pa).

In some embodiments, the silicone is chosen from liquid polydialkylsiloxanes, especially liquid polydimethylsiloxanes (PDMSs) and liquid polyorganosiloxanes comprising at least one aryl group.

These silicones may also be organomodified. The organomodified silicones that can be used are liquid silicones as defined above and comprising in their structure one or more organofunctional groups attached via a hydrocarbon-based group. They may be volatile or non-volatile. When they are volatile, the silicones are more particularly chosen from those having a boiling point of between 60° C. and 260° C., and more particularly still from:

(i) cyclic polydialkylsiloxanes comprising from 3 to 7, including 4 to 5 silicon atoms;

(ii) linear volatile polydialkylsiloxanes containing 2 to 9 silicon atoms and having a viscosity of less than or equal to $5 \times 10^{-6}$ m$^2$/s at 25° C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups. There is also polydimethylsiloxanes containing dimethylsilanol end groups known under the name Dimethiconol (CTFA).

The organomodified liquid silicones may especially contain polyethyleneoxy and/or polypropyleneoxy groups.

Composition according to the invention may also comprise non-liquid fatty substances at room temperature and at atmospheric pressure.

The term "non-liquid" generally means a solid compound or a compound that has a viscosity of greater than 2 Pa·s at a temperature of 25° C. and at a shear rate of 1 s$^{-1}$.

More particularly, the non-liquid fatty substances are chosen from fatty alcohols, esters of fatty acids and/or of fatty alcohols, non-silicone waxes, silicones and fatty ethers, which are non-liquid and such as solid.

The non-liquid fatty alcohols may be chosen from saturated or unsaturated, linear or branched alcohols comprising from 8 to 30 carbon atoms, for example, of cetyl alcohol, stearyl alcohol and a mixture thereof (such as cetylstearyl alcohol).

In some embodiment, the non-liquid fatty alcohol of the invention is cetylstearyl alcohol.

As regards the non-liquid esters of fatty acids and/or of fatty alcohols, there is especially of solid esters derived from $C_9$-$C_{26}$ fatty acids and from $C_9$-$C_{26}$ fatty alcohols. Among these esters, mention may be made of octyldodecyl behenate; isocetyl behenate; cetyl lactate; stearyl octanoate; octyl octanoate; cetyl octanoate; decyl oleate; myristyl stearate; octyl palmitate; octyl pelargonate; octyl stearate; alkyl myristates such as cetyl, myristyl or stearyl myristate; hexyl stearate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used. There is also diethyl sebacate; diisopropyl sebacate; diisopropyl adipate; di-n-propyl adipate; dioctyl adipate; dioctyl maleate.

Among all the additional esters mentioned above, in some embodiments, one can use myristyl, cetyl or stearyl palmitates, alkyl myristates such as cetyl myristate, and stearyl myristyl myristate.

The (non-silicone) wax(es) may be selected from carnauba wax, candelilla wax, esparto grass wax, paraffin wax, ozokerite, plant waxes such as olive wax, rice wax, hydrogenated jojoba wax or the absolute waxes of flowers, animal waxes, for instance beeswaxes or modified beeswaxes (cerabellina).

Composition according to the invention may comprise non-liquid silicones in the form of waxes, resins or gums.

The non-liquid silicone may be chosen from polydialkylsiloxanes, especially polydimethylsiloxanes (PDMS), and organomodified polysiloxanes comprising at least one functional group chosen from poly(oxyalkylene) groups, amino groups and alkoxy groups.

The silicone gums are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

The non-liquid fatty ethers may be chosen from dialkyl ethers and especially dicetyl ether and distearyl ether, alone or as a mixture.

In some embodiments, the fatty substances used in the composition according to the invention do not comprise any oxyalkylene units or any glycerol units.

In some embodiments, the fatty substances free of carboxylic acid groups used in the composition are selected from the group consisting of liquid paraffins, liquid petroleum jelly, polydecenes, liquid fatty acid esters, liquid fatty alcohols such as octyldodecanol or non-liquid fatty alcohols such as cetylstearyl alcohol, and mixtures thereof.

In some embodiments, the fatty substances free of carboxylic acid groups are selected from the group consisting of liquid petroleum jelly, liquid fatty alcohols such as octyldodecanol or non-liquid fatty alcohols such as cetylstearyl alcohol, and mixtures thereof.

In some embodiments, the composition according to the invention contains one or more fatty substances that are liquid at room temperature (25° C.) and at atmospheric pressure (760 mmHg; i.e. $1.013 \times 10^5$ Pa), optionally combined with one or more fatty substances that are non-liquid under the same conditions.

The composition according to the invention comprises an amount of fatty substances free of carboxylic acid groups of at least 25%, such as of at least 30%, including of at least 40% by total weight of the composition.

In some embodiments, the concentration of fatty substances free of carboxylic acid groups ranges from 25% to 85%, more such as from 25% to 60%, including from 30% to 55% by total weight of the composition.

Alkalizing Agents

The composition according to the present invention can comprise comprises at least one alkalizing agents.

By "alkalising agent", it is meant one or more compounds suitable for increasing the pH to alkaline levels. That is to say, the alkalising agent(s) is (are) generally such that the $pK_b$ at 25° C. is less than 12, such as less than 10 and more advantageously less than 6. Generally, the most commonly used alkalising agent in the art is ammonia. Non-ammonia alkalising agents are also known and advantageous in view of reduced olfactory stimulation, e.g. alkanolamines.

Suitable alkalizing agents include, but are not limited to: ammonia; alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine.

The composition of the invention may comprise one or more non-ammonia alkalizing agents selected from the group consisting of: monoethanolamine (MEA), sodium silicate, sodium meta silicate, diethanolamine, triethanolamine, monopropanolamine, dipropanolamine, tripropanolamine, 2-amino-2-methyl-1,3-propanediol, 2-amino-2-methyl-1-propanol (a.k.a. aminomethylpropanol, AMP), 2-amino-2-hydroxymethyl-1,3-propanediol, and mixtures thereof.

Monoethanolamine (MEA) or aminomethylpropanol (AMP) are commonly used in ammonia-free hair dye products.

In some embodiments, the alkalising agent is monoethanolamine (MEA) alone or in combination with other alkalizing agents.

Monoethanolamine may in particular can be to be used alone or in combination with other non-ammonia alkalising agent.

In some embodiments, the composition according to the invention may not comprise any aqueous ammonia or salts thereof as alkalising agent. If, however, it did comprise any, its content would not exceed 0.03% by weight, including not exceed 0.01% by weight relative to the weight of the composition of the invention.

In some embodiments, if the composition comprises aqueous ammonia or a salt thereof, then the amount of non-ammonia alkalising agent is greater than the amount of aqueous ammonia.

The composition may comprise an alkalising agent which is monoethanolamine (MEA) and a primary intermediate which is 2-methoxymethyl-1,4-benzenediamine.

The composition of the invention may comprise a total amount of alkalizing agents ranging from 0.01% to 10%, such as from 0.1% to 8%, including from 0.1% to 5% by total weight of the composition.

The composition of the invention may comprise a total amount of alkalizing agents of less than 10%, such as less than 8%, including less than 5% by total weight of the composition.

Oxidative Dye/Direct Dye

The composition of the invention may optionally comprise at least one dye chosen from oxidative dyes precursors, direct dyes or mixture thereof.

The composition of the invention may comprise at least one oxidative dye precursor, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

In some embodiments, the composition of the invention comprises at least two oxidative dye precursors comprising one or more primary intermediates and one or more couplers.

The oxidative dye precursors suitable for use herein, in so far as they are bases, may be used as free bases or in the form of any cosmetically acceptable salts obtained with the corresponding organic or inorganic acids, such as hydrochloric, hydrobromic, citric, acetic, lactic, succinic, tartaric, or sulfuric acids, or, in so far as they have aromatic hydroxyl groups, in the form of any cosmetically acceptable salts obtained with the corresponding bases, such as alkali phenolates.

Oxidative dye precursors are known in the art, and include aromatic diamines, aminophenols, aromatic diols and their derivatives (a representative but not exhaustive list of oxidation dye precursors can be found in Sagarin, "Cosmetic Science and Technology", Interscience, Special Edn. Vol. 2 pages 308 to 310). Suitable oxidative dye precursors are also disclosed in the Canadian Patent Application No. CA2576189A1—in particular, from Table 1 dye combinations No. 1 to 2394, which span pages 49 to 238, are incorporated herein by reference. It is to be understood that the one or more primary intermediates and the one or more couplers (collectively known as oxidative dye precursors) detailed below are only by way of example and are not intended to limit the compositions and other aspects herein described. The one or more primary intermediates and the one or more couplers may be used in the form of any cosmetically acceptable salts, for example sulfate salts.

The one or more primary intermediates may be selected from the group consisting of toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino) phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, their salts thereof and mixtures thereof.

The one or more primary intermediate of the composition may be particularly 1,4-diamino-2-(methoxymethyl)-benzene. 1,4-diamino-2-(methoxymethyl)-benzene has the advantage of an improved sensitisation profile (i.e. reduced risks of scalp skin reaction).

The one or more primary intermediate may be 4,5-diamino-1-hexylpyrazole. 4,5-diamino-1-hexylpyrazole used as a sulfate salt.

The one or more primary intermediate may be selected from the group consisting of 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, and mixtures thereof; and the cosmetically acceptable salts thereof such as chlorides, sulfates and hemi-sulfates in particular.

The one or more couplers may be a compound comprising one or more phenyl rings substituted with one or more hydroxyl groups.

The one or more couplers may be selected from the group consisting of resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The oxidative dye precursors may be particularly selected from the group consisting of I-naphthol, 2,4-diaminophenoxyethanol, toluene-2,5-diamine sulfate, resorcinol, 4-amino-m-cresol, 2-amino-4-hydroxyethylaminoanisole sulfate, N,N-bis(2-hydroxyethyl)-p-phenylenediamine, hydroxyethyl-3,4-methylenedioxyaniline HCl, 1-hydroxyethyl 4,5-diamino pyrazole sulfate, 4-amino-2-hydroxytoluene, p-aminophenol, 2-methoxymethyl-p-phenylenediamine 2-methylresorcinol, m-aminophenol, 2-methyl-5-hydroxyethylaminophenol, and mixtures thereof.

Preferably, the primary intermediates are selected from the group consisting of toluene-2,5-diamine, 2-methoxymethyl-p-phenylenediamine, N,N-bis(2-hydroxyethyl)-p-phenylenediamine, p-aminophenol and mixtures thereof.

Preferably, the couplers are selected from the group consisting of resorcinol, methylresorcinol, naphthol, m-aminophenol, 4-amino-2-hydroxytoluene, 2-methyl-5-hydroxyethylaminophenol, 2,4-diaminophenoxyethanol, 2-amino-4-hydroxyethylaminoanisole and mixtures thereof.

The composition according to the present invention may further comprise compatible direct dyes, in an amount sufficient to provide additional colouring, particularly with regard to intensity. The composition may further comprise one or more direct dyes, advantageously one or more oxidatively stable direct dyes.

Typically, compositions of the invention may comprise a total amount of direct dyes ranging from 0.001% to 2.8%, including from 0.005% to 0.1.5%, such as from 0.01% to 0.5%, by total weight of the composition.

The presence of one or more direct dyes and the proportion thereof can help to provide or enhance colouring/dyeing, particularly with regard to the vibrancy of the color that is desired.

IN some embodiments, the composition of the invention is substantially free of any direct dyes. Indeed, sometimes consumers prefer direct dye-free compositions.

The one or more direct dyes may be selected from the group consisting of nitro dyes to provide a blue color, nitro dyes to provide a red color or a yellow color, quinone dyes, basic dyes, neutral azo dyes, acid dyes, and mixtures thereof. The one or more direct dyes may be a basic dye. The one or more direct dyes may be a neutral azo dye. The one or more direct dyes may be an acid dye.

The one or more direct dyes may be selected from the group consisting of Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methyl-morpholin-4-ium-methylsulfate, (E)-1-(2-(4-(4,5-dimethyl-thiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, 2-amino-6-chloro-4-nitrophenol, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14, Natural dyes such as Annato, Anthocyanin, Beetroot, Carotene, Capsanthin, Lycopene, Chlorophyll, Henna, Indigo, Cochineal; and mixtures thereof.

The level of oxidative dye precursors used in the composition of the invention is described herein with reference of the level of primary intermediates within the composition. This proves a useful reference, as it's generally considered that the level of primary intermediates dictates the level of color formed. Whilst not wishing to be bound to theory, it's believed that the rate limiting step during color formation is the oxidation of the primary intermediate, with the subsequent coupling reactions occurring rapidly. As the primary intermediates have different chemical structures, and for some the primary intermediate is also available either as pure materials or in the form of various salts, it's not practical to consider the amount of primary intermediate simply in terms of weight added to the composition. The following expression is used to calculate the level of primary intermediates within the composition such that it's expressed in terms of molar concentrations.

$$\text{mM dyes/Kg composition} = 1000 * \sum_{n=1}^{n=n} \frac{10*(\text{wt \% primary intermediate})_n}{\text{molecular weight primary intermediate}_n}$$

Wherein the wt % of the primary intermediate refers to the level in the final composition, the molecular weight refers to the primary intermediate used and when multiple primary intermediates are used, the suffix n refers to each primary intermediate within the composition.

Surfactants

The composition of the invention can comprise at least one surfactant. A surfactant can help to provide an emulsion.

The composition of the invention may comprise from 0.1% to 20%, including from 0.1% to 15%, such as from 0.2% to 12%, or from 0.5% to 10% of surfactants by total weight of the composition.

In some embodiments, the composition of the invention comprises one or more surfactants selected from the group consisting of anionic surfactants, non-ionic surfactants, amphoteric surfactants, zwitterionic surfactants, cationic surfactants, and mixtures thereof.

The one or more surfactants of the composition can be useful for stabilising a hydrophobic phase in the composition, e.g. for stabilising the gel network and/or lamellar structure.

The composition of the invention may comprise an anionic surfactant. The anionic surfactants may be selected from the group consisting of salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Suitable anionic surfactant(s) may comprise at least one anionic functional groups at their head selected from sulfate, sulfonate, phosphate and carboxylates.

Suitable alkyl sulfates include ammonium lauryl sulfate, sodium lauryl sulfate (sodium dodecyl sulfate, SLS, or SDS), and alkyl-ether sulfates, such as sodium laureth sulfate (sodium lauryl ether sulfate or SLES), and sodium myreth sulfate.

Further suitable anionic surfactants may include Docusate (dioctyl sodium sulfosuccinate), alkyl-aryl ether phosphate, alkyl ether phosphate, alkyl carboxylate, such as sodium stearate, sodium lauroyl sarcosinate, ammonium laureth sulfate, disodium lauryl sulfosuccinate, and sodium lauryl sulphoacetate.

In some embodiments, anionic surfactants may be selected from the group consisting of sodium laurylethersulfate, sodium laurethethersulfate, sodium dodecyl sulfate, ammonium laurethethersulfat, ammonium dodecyl sulfate, alkylbenzenesulfonate, and combinations thereof.

The one or more surfactants of the composition of the invention may be non-ionic surfactants. The non-ionic surfactant(s) may be selected from the group consisting of lanolin alcohol, and polyoxyethylene ethers of fatty alcohols, and mixtures thereof. The non-ionic surfactant may be preferably ceteareth-n, wherein n is from 2 to 100, or from 10 to 30. When the one or more surfactants of the composition are non-ionic, precipitation of other ingredients of the composition can be prevented. Suitable nonionic surfactants are compounds that are well known (see, for example, in this respect "Handbook of Surfactants" by M. R. Porter, published by Blackie & Son (Glasgow and London), 1991, pp. 116-178).

The nonionic surfactants are more particularly chosen from monooxyalkylenated or polyoxyalkylenated, monoglycerolated or polyglycerolated nonionic surfactants. The oxyalkylene units are more particularly oxyethylene or oxypropylene units, or a combination thereof, such as POE/POP/POE (INCI: Poloxamer 184) (Trade Name: Pluracare L64, BASF), such as oxyethylene units.

Examples of oxyalkylenated nonionic surfactants include:
oxyalkylenated ($C_8$-$C_{24}$)alkylphenols,
saturated or unsaturated, linear or branched, oxyalkylenated $C_8$-$C_{30}$ alcohols such as oxyethylenated cetylstearyl alcohol (33OE) or oleyl alcohol (10OE),
saturated or unsaturated, linear or branched, oxyalkylenated $C_5$-$C_{30}$ amides,
esters of saturated or unsaturated, linear or branched, $C_8$-$C_{30}$ acids and of polyethylene glycols,
polyoxyethylenated esters of saturated or unsaturated, linear or branched, $C_8$-$C_{30}$ acids and of sorbitol,
saturated or unsaturated, oxyethylenated plant oils,
condensates of ethylene oxide and/or of propylene oxide, and mixtures thereof.

These surfactants contain a number of moles of ethylene oxide and/or of propylene oxide of between 1 and 100 and preferably between 2 and 50. Advantageously, the nonionic surfactants do not comprise any oxypropylene units.

In some embodiments, the oxyalkylenated nonionic surfactants are chosen from oxyethylenated $C_8$-$C_{30}$ alcohols, and esters of $C_8$-$C_{30}$ acids and of polyethylene glycols.

As examples of monoglycerolated or polyglycerolated nonionic surfactants, monoglycerolated or polyglycerolated $C_8$-$C_{40}$ alcohols are preferably used. In particular, the monoglycerolated or polyglycerolated $C_8$-$C_{40}$ alcohols correspond to the following formula:

in which R represents a linear or branched $C_8$-$C_{40}$ and preferably $C_8$-$C_{30}$ alkyl or alkenyl radical, and m represents a number ranging from 1 to 30, such as from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

Among the monoglycerolated or polyglycerolated alcohols, it is more particularly preferred to use the $C_8$-$C_{10}$ alcohol containing 1 mol of glycerol, the $C_{10}$-$C_{12}$ alcohol containing 1 mol of glycerol and the $C_{12}$ alcohol containing 1.5 mol of glycerol.

In some embodiment's, the non-ionic surfactants of the composition of the invention are selected from the group consisting of POE/POP/POE (INCI: Poloxamer 184), oxyethylenated $C_8$-$C_{30}$ alcohols such as oxyethylenated cetylstearyl alcohol (33OE) or oleyl alcohol (10OE), esters of $C_8$-$C_{30}$ acids and of polyethylene glycols, and mixtures thereof.

In some embodiments, the non-ionic surfactants of the composition of the invention are selected from the group consisting of POE/POP/POE (INCI: Poloxamer 184) or oxyethylenated $C_8$-$C_{30}$ alcohols, such as oxyethylenated cetylstearyl alcohol (33 OE) or oleyl alcohol (10OE) and mixtures thereof.

In some embodiments, the surfactants of the composition of the invention are selected from the group consisting of non-ionic surfactants, anionic surfactants and mixtures thereof, such as, the surfactants of the composition are non-ionic surfactants.

Thickeners

The composition of the invention may also comprise one or more thickeners.

These thickeners may be chosen from fatty acid amides (coconut acid diethanolamide or monoethanolamide, oxyethylenated alkyl ether carboxylic acid monoethanolamide), polymeric thickeners such as cellulose-based thickeners (hydroxyethyl cellulose, hydroxypropylcellulose, carboxymethylcellulose), guar gum and derivatives thereof (hydroxypropylguar), fumed silicas, and clays, especially bentonites and hectorites, and derivatives thereof.

The content of thickener(s), if they are present, usually ranges from 0.01° % to 20% and preferably from 0.1% to 5% by total weight of the composition.

The clay may be organically modified clay mineral. The organically modified clay mineral is used as an emulsion aid.

The organically modified clay mineral is a type of colloidal aluminum silicate hydrate that has a three-layer structure that is prepared by modifying a clay mineral with a quaternary ammonium salt cationic surfactant. For example, organically modified bentonite and organically modified hectorite can be used.

Specific examples include dimethyldistearyl ammonium hectorite, dimethyl alkyl ammonium hectorite, benzyl dimethyl stearyl ammonium hectorite, and aluminum magnesium silicate treated with distearyl dimethyl ammonium chloride.

In some embodiments, the thickener are clays such as dimethyldistearyl ammonium hectorite.

In some embodiments, the thickener used in the composition of the invention is dimethyldistearyl ammonium hectorite.

Chelants

The composition of the invention may further comprise one or more chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and AE Martell & RD Hancock, Metal Complexes in Aqueous Solution, Plenum Press, New York & London (1996), both incorporated herein by reference.

The composition of the invention may comprise a total amount of chelants ranging from at least 0.01%, such as from 0.01% to 5%, including from 0.1% to 3%, including from 0.25% to 1%, by total weight of the composition.

The one or more chelants may be selected from the group consisting of carboxylic acids (such as aminocarboxylic acids), phosphonic acids (such as aminophosphonic acids), polyphosphoric acids (such as linear polyphosphoric acids), their salts thereof, and mixtures thereof.

By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, calcium salts, magnesium salts, ammonium salts, and mixtures thereof; alternatively monoethanolammonium salts, diethanolammonium salts, triethanolammonium salts, and mixtures thereof.

The one or more chelants may be one or more aminocarboxylic acid chelants comprising one or more carboxylic acid moieties (—COOH) and one or more nitrogen atoms. The one or more aminocarboxylic acid chelants may be selected from the group consisting of diethylenetriamine pentaacetic acid (DTPA), diethylenetriamine-N,N',N''-polyacids, ethylenediamine disuccinic acid (EDDS), ethylenediamine-N,N'-diglutaric acid (EDDG), 2-hydroxypropylenediamine-N—N'-disuccinic acid (HPDDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis (2-hydroxybenzyl)ethylenediamine-N,N'-diacetic acid (HBED), ethylene diamine tri(methylene phosphonate), hexamethylene diamine tetra (methylene phosphonate), their salts thereof, and mixtures thereof.

Alternatively, the one or more aminocarboxylic acid chelants may be selected from the group consisting of iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, dipicolinic acid, 2-phosphonobutane-1,2,4-tricarboxylic acid their salts thereof, their derivatives thereof, and mixtures thereof.

The one or more chelants may be one or more aminophosphonic acid chelants comprising an aminophosphonic acid moiety (—PO$_3$H$_2$) or its derivative—PO3R$_2$, wherein R$_2$ is a C$_1$ to C$_6$ alkyl or aryl radical and salts thereof.

The one or more aminophosphonic acid chelants may be selected from the group consisting of aminotri-(1-ethylphosphonicacid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N''-ethylenediamine diacetic acid, their salts thereof, their derivatives thereof, and mixtures thereof.

Other various chelants may also be contemplated, including the amino phosphonates, available as Dequest® from Monsanto, the nitriloacetates, the hydroxyethyl-ethylene triamines and the like which are known for such use. Suitable chelants for use herein may include organic phosphonates, such as the amino alkylene poly (alkylene phosphonates), alkali metal ethane 1-hydroxy disphosphonates and nitrilo trimethylene phosphonates.

In some embodiments, the composition of the invention comprises a chelant selected from the group consisting of diethylenetriamine-N,N',N''-polyacids, diethylenetriamine-pentaacetic acid (DTPA), diethylenetriaminepenta(methylene phosphonic acid) (DTPMP), ethylene diamine tri(methylene phosphonate), hexamethylene diamine tetra (methylene phosphonate), ethylenediaminedisuccinic acid (EDDS), their salts thereof, their derivatives thereof, and mixtures thereof.

Organic Solvents

The composition of the invention may further comprise one or more organic solvents.

The one or more organic solvents may be selected to dissolve the compounds that would not typically be sufficiently soluble in water.

Suitable organic solvents include, but are not limited to: C$_1$ to C$_4$ lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol, monoethyl ether, monomethyl ether, hexylene glycol, glycerol, ethoxy glycol, butoxydiglycol, ethoxydiglycerol, dipropyleneglycol, polygylcerol); propylene carbonate; and mixtures thereof.

In some embodiments, the one or more solvents are selected from the group consisting of ethanol, propanol, isopropanol, glycerol, propylene glycol, hexylene glycol, dipropyleneglycol, propylene carbonate, and mixtures thereof.

The composition of the invention may comprise a total amount of organic solvents ranging from 0.11% to 20% by weight, such as from 1% to 10% by weight relative to the total weight of the composition.

Water

According to the invention, the composition may comprise an amount of water greater than 2% by weight, such as greater than 5% by weight relative to the total weight of the composition.

The composition of the invention may comprise less than 80% by weight of water, such as less than 50% by weight of water, including between 5% and 50% by weight of water relative to the total weight of the composition.

pH Modifiers

According to the invention, the composition may further comprise a pH modifier in an amount that is sufficiently effective to adjust the pH of the composition to fall within a range prescribed above.

Suitable pH modifiers for use herein may include, but are not limited to ammonia, acidulents (such as inorganic and inorganic acids including for example phosphoric acid, acetic acid, ascorbic acid, citric acid or tartaric acid, hydrochloric acid); alkanolamines (such as monoethanolamine, diethanolamine, triethanolamine, monopropanolamine, dipropanolamine, tripropanolamine, 2-amino-2-methyl-1-propanol, and 2-amino-2-hydroxymethyl-1,3-propanediol); guanidium salts, alkali metal such as sodium hydroxide, tetrasodium pyrophosphate or ammonium hydroxides and carbonates; and mixtures thereof.

The pH of the composition according to the invention may be from 3 to 12, such as from 5 to 11, including from 7 to 11.

Oxidizing Agent(s)

The composition according to the invention can comprise at least one oxidizing agent. As used herein, "water-soluble" means that in standard conditions at least 0.1 g, such as 1 g, including 10 g of the oxidizing agent can be dissolved in 1 litre of deionized water at 25° C. Suitable water-soluble oxidizing agents include but are not limited to: inorganic peroxygen materials capable of yielding hydrogen peroxide in an aqueous solution.

The one or more oxidizing agents are valuable for the initial solubilization and decolorization of the melanin (bleaching) and accelerate the oxidation of the oxidative dye precursors (oxidative dyeing) in the hair shaft.

Suitable water-soluble peroxygen oxidizing agents include but are not limited to: hydrogen peroxide; inorganic alkali metal peroxides (such as sodium periodate and sodium peroxide); alkali metal bromates or ferricyanides, organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used.

The percarbonates may be used to provide a source of both oxidizing agent and carbonate ions and or ammonium ions.

The oxidizing agent(s) may be selected from the group consisting of hydrogen peroxide, urea peroxide and their salts thereof, and inorganic perhydrate salts, for instance alkali metals or alkaline-earth metals salts, such as sodium, potassium or magnesium, of persulfates, perborates and percarbonates, and mixtures thereof.

In some embodiments, the composition of the invention comprises an oxidizing agent selected from the group consisting of hydrogen peroxide, percarbonates, persulphates, and mixtures thereof.

In other embodiments, oxidizing agent is hydrogen peroxide.

A composition of the invention for lightening keratin fibers can have a concentration of oxidizing agent in the composition from 1.5% to 2.5% by weight relative to the total weight of the composition.

The concentration of oxidizing agent in the composition may be from 1.5% to 2.3% by weight, such as from 1.5% to 2.2% by weight relative to the total weight of the composition.

Alternatively, the total amount of oxidizing agents in the composition may be at least 1.5% and not more than 2.3% by weight, alternatively not more than 2.2% by weight, alternatively not more than 2.1% by weight relative to the total weight of composition.

Conditioning Agents

The composition according to the invention may further comprise at least one conditioning agent.

Typically, the composition may comprise a total amount of conditioning agents ranging from 0.05% to 10%, such as from 0.1% to 8%, including from 0.1% to 5%, including from 0.1% to 2% by total weight of the composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials, mineral oils and other oils such as glycerin and sorbitol and mixtures thereof.

The cationic polymers may be selected from polymers of polyamine, polyamino amide and polyquaternary ammonium type, such as cyclopolymers of dialkdiallylamine or of dialkyldiallyammonium, including: dimethyldiallyammonium chloride polymers, such as polymers known as Polyquaternium-6.

In some embodiments, the conditioning agent is a cationic polymer chosen from the group of cyclopolymers of dialkyldiallylamine or of dialkyldiallyammonium, such as dimethyldiallyammonium chloride polymers.

Other Ingredients

According to the invention, the composition may comprise, in addition to the ingredients indicated above, further ingredients in order to further enhance the properties of the composition, as long as these are not excluded by the claims.

Suitable further ingredients include, but not limited to: anionic, cationic, nonionic, amphoteric or zwitterionic polymers or mixtures thereof, antioxidants, pigment, penetrating agents, sequestrants, perfumes, dispersing agents, film-forming agents, cosmetically acceptable carrier, radical scavengers, ceramides, preservatives, opacifying agents and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Figure 10:
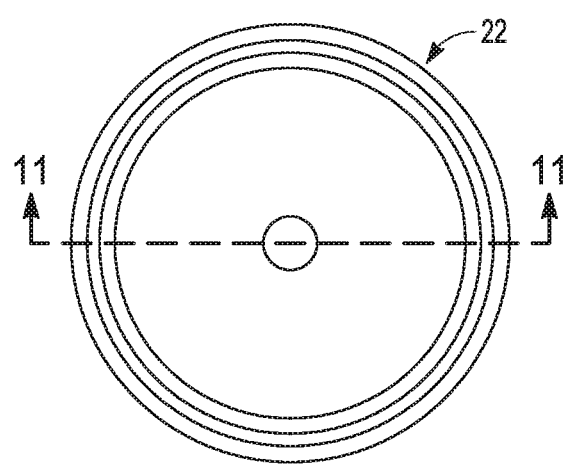
FIG. 10 is bottom view of the cap of FIGS. 2 and 3.
Figure 11:
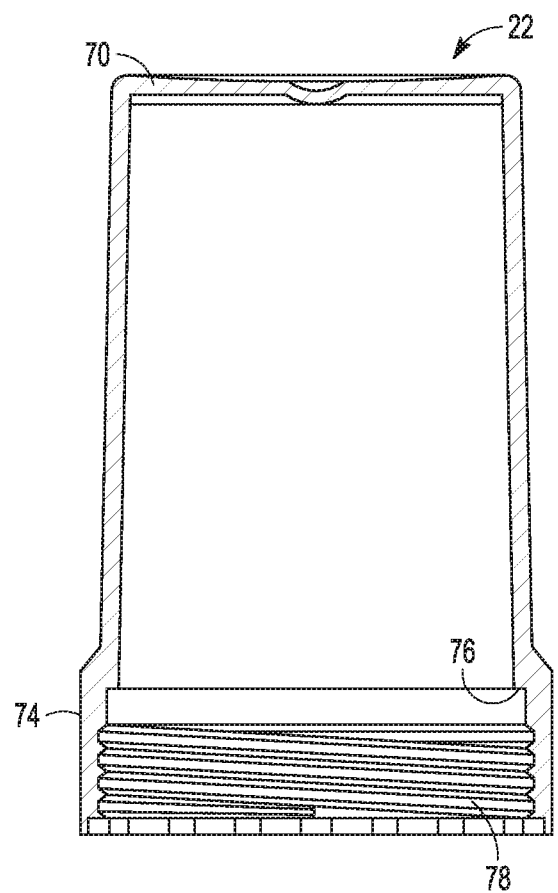
FIG. 11 is a side cross-sectional view of the cap of FIG. 10 taken at section 11-11.

FIG. 10 is bottom view of cap 22 of FIGS. 2 and 3. FIG. 11 is a side cross-sectional view of cap 22 of FIG. 10 taken at section 11-11. FIGS. 10 and 11 are discussed concurrently. Cap 22 can comprise end wall 70, side wall 72, flange 74, actuator ledge 76 and thread 78. Cap 22 can be made of any suitable material that provides protection for brush 24 and that can prevent air or oxygen from passing through cap 22. In examples, cap 22 can be made of a rigid material to provide strength for thread 78. In an example, thread 78 can comprise female thread or channels into which male thread, such as thread 54 (FIGS. 8 and 9) of tube head 14 can be engaged.

Figure 14:
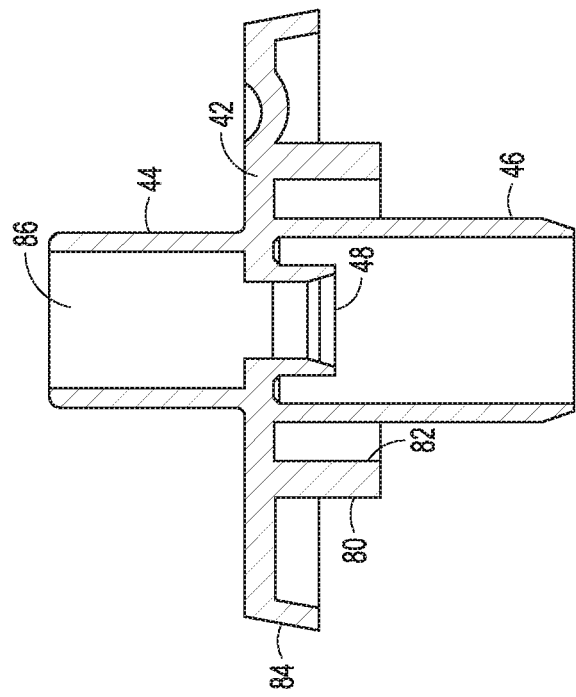
FIG. 14 is a side cross-sectional view of the brush valve of FIG. 12.
Figure 12:
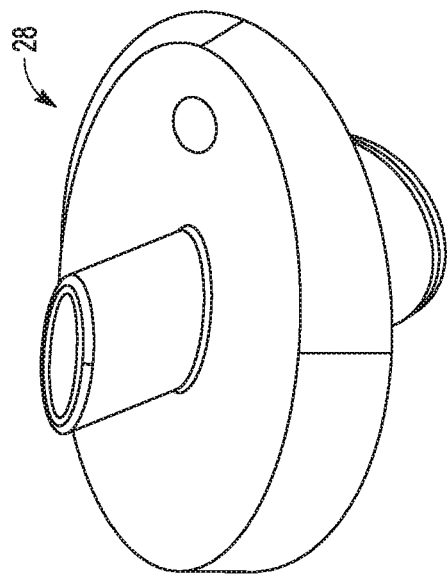
FIG. 12 is a perspective view of the brush valve of FIGS. 4-6 showing a discharge stem and a slide post.
Figure 13:
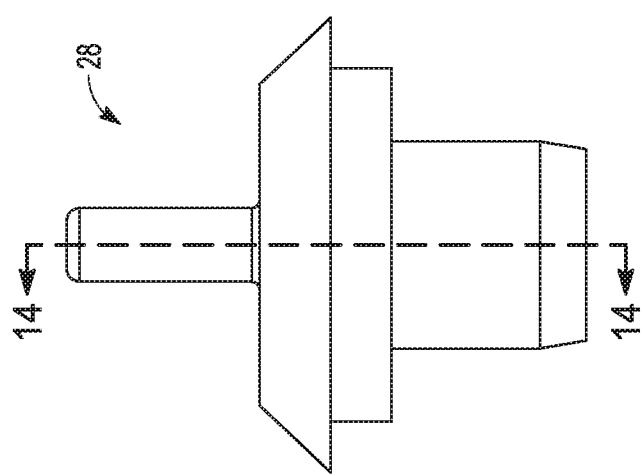
FIG. 13 is a side view of the brush valve of FIG. 12.

FIG. 12 is a perspective view of brush valve 28 of FIGS. 4-6 showing discharge stem 44 and slide post 46. FIG. 13 is a side view of brush valve 28 of FIG. 12. FIG. 14 is a side cross-sectional view of brush valve 28 of FIG. 12. FIGS. 12-14 are discussed concurrently. Brush valve 28 can comprise nozzle flange 80, nozzle pocket 82, holder flange 84 and passage 86.

Brush valve 28 can be made of any suitable material that provides support for brush 24 and that can prevent air or oxygen from passing into tube 12. In examples, brush valve 28 can be made of a rigid material to provide strength for base 42 and holder flange 84. In an example, brush valve 28 can be made of HDPE.

Figure 15:
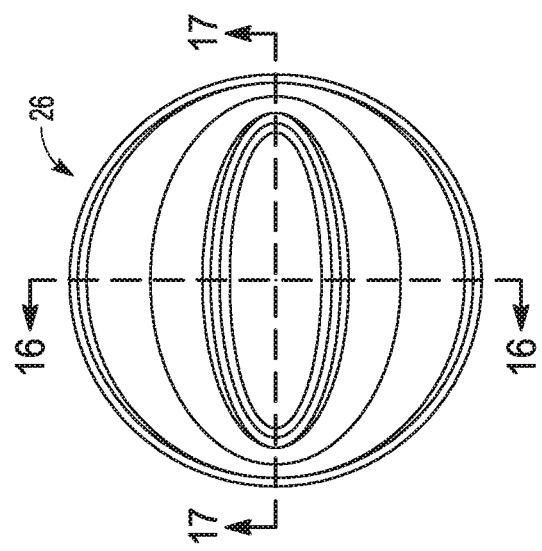
FIG. 15 is a top view of a brush holder of the brush assembly of FIGS. 4-6.
Figure 17:
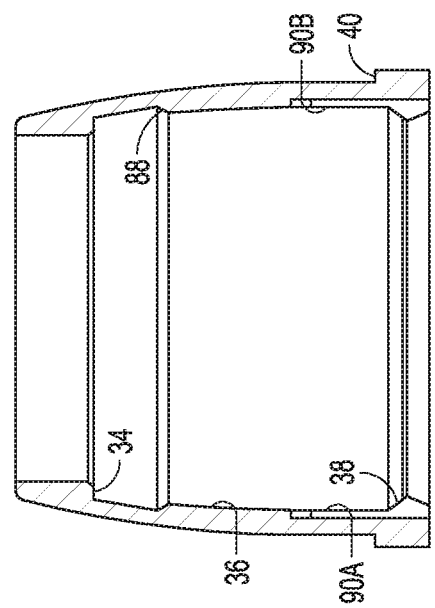
FIG. 17 is a cross-sectional view of the brush holder of FIG. 15 taken at section 17-17 to show a width of a brush opening.
Figure 16:
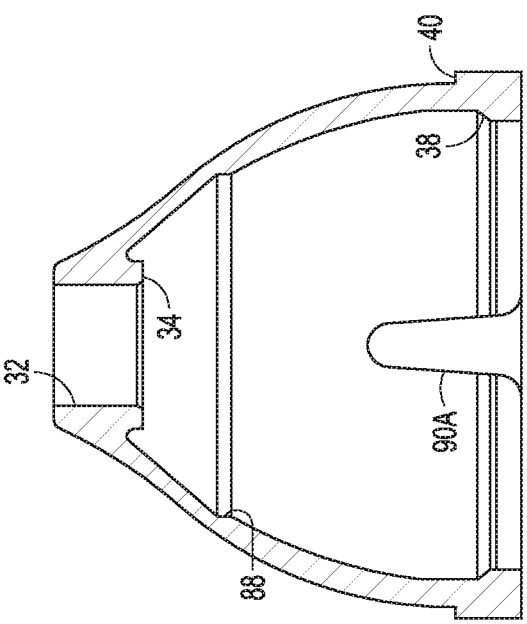
FIG. 16 is a cross-sectional view of the brush holder of FIG. 15 taken at section 16-16 to show a thickness of a brush opening.

FIG. 15 is a top view of brush holder 26 of brush assembly 20 of FIGS. 4-6. FIG. 16 is a cross-sectional view of brush holder 26 of FIG. 15 taken at section 16-16. FIG. 17 is a cross-sectional view of brush holder 26 of FIG. 15 taken at section 17-17. FIGS. 15-17 are discussed concurrently. Brush holder 26 can comprise brush socket 32, brush ledge 34, chamber 36, flange 38, cap ledge 40, base notch 88 and rail slots 90A and 90B.

Brush holder 26 can be made of any suitable material that provides support for brush 24 and that can prevent air or oxygen from passing into tube 12. In examples, brush holder 26 can be made of a rigid material to provide strength for brush socket 32, brush ledge 34, chamber 36, flange 38, cap ledge 40, base notch 88 and rail slots 90A and 90B.

Tube head 14, cap 22, brush holder 26 and brush valve 28 can be made of any suitable material. In examples, tube head 14, cap 22, brush holder 26 and brush valve 28 can be made of the same material as tube 12. In additional examples, tube head 14, cap 22, brush holder 26 and brush valve 28 can be made of Polyethylene terephthalate (PET), Polyethylene (PE), High-density polyethylene (HDPE), Polyvinyl chloride (PVC), Polyvinylidene chloride (PVDC) (Saran), Low-density polyethylene (LDPE), Polypropylene (PP), Polystyrene (PS), High impact polystyrene (HIPS), Polyamides (PA) (Nylons), Acrylonitrile butadiene styrene (ABS), Polyethylene/Acrylonitrile Butadiene Styrene (PE/ABS), Polycarbonate (PC), Polycarbonate/Acrylonitrile Butadiene Styrene (PC/ABS), Polyurethanes (PU), Acrylonitrile butadiene styrene (ABS), Acrylic, Celluloid, Cellulose acetate, Ethylene-Vinyl Acetate (EVA), Ethylene vinyl alcohol (EVAL), Fluoroplastics (PTFEs, including FEP, PFA, CTFE, ECTFE, ETFE), Ionomers, Kydex, a trademarked acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA or Nylon), Polyamide-imide (PAI), Polyaryletherketone (PAEK or Ketone), Polybutadiene (PBD), Polybutylene (PB), Polybutylene terephthalate (PBT), Polyethylene terephthalate (PET), Polycyclohexylene dimethylene terephthalate (PCT), Polycarbonate (PC), Polyhydroxyalkanoates (PHAs), Polyketone (PK), Polyester, Polyethylene (PE) including low density (LDPE) and high density (HDPE) versions, Polyetheretherketone (PEEK), Polyetherimide (PEI), Polyethersulfone (PES)—see Polysulfone, Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polypropylene (PP), Polystyrene (PS), Polysulfone (PSU), Polyvinyl chloride (PVC), Polyvinylidene chloride (PVDC), Spectralon. Most preferred are polyolefins, and in particular polyethylene, polyethylene terephthalate, polypropylene, or mixtures thereof.

Figures 18, 19:
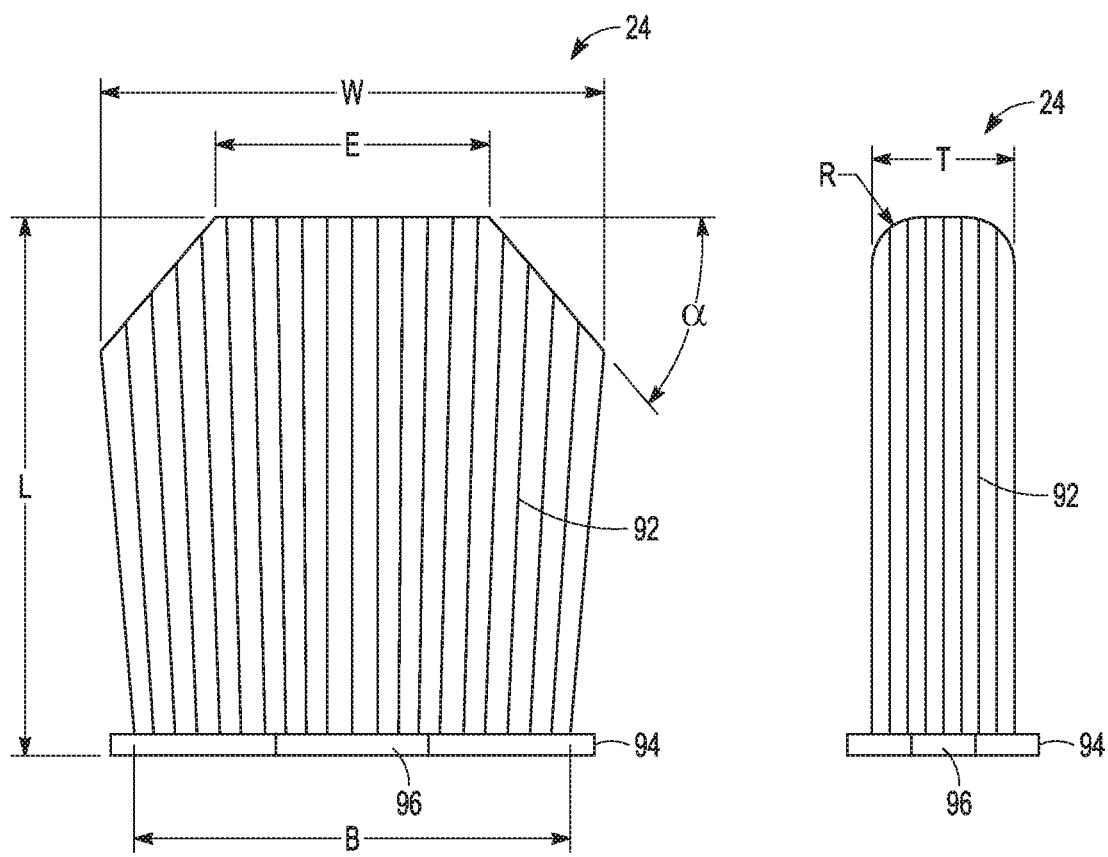
FIG. 18 is a side view of a brush of the brush assembly of FIGS. 4-6 showing a width of the brush.
FIG. 19 is a side view of the brush of the brush assembly of FIGS. 4-6 showing a thickness of the brush.

FIG. 18 is a side view of brush 24 of brush assembly 20 of FIGS. 4-6. FIG. 19 is a transverse side view of brush 24 of brush assembly 20 of FIGS. 4-6. FIGS. 18 and 19 are discussed concurrently. Brush 24 can comprise bristles 92 and baseplate 94. Baseplate 94 can include aperture 96. Bristles 92 can be made of any suitable brush material, including synthetic and naturally occurring materials, such as animal hairs. In an example, bristles 92 can be made of Polybutylene Terephthalate (PBT). The present inventors have found that synthetic bristles are more suitable for use with semi-permanent oxidative or direct dye hair coloring compositions. Bristles 92 can be integrally formed with baseplate 94. In an example, bristles 92 can be bonded to baseplate 94 such as during a manufacturing process that simultaneously or contemporaneously forms bristles 92 and baseplate 94.

Brush 24 comprises one of a plurality of applicator heads that can be used with hair dye applicator device 10. In examples, other types of applicator heads that can be used with the present disclosure can include sponges, non-woven material, woven material and combs. In examples, detachable, telescoping, flexible and hinged applicator heads can be used.

Brush 24 can be shaped to facilitate a user applying the hair dye composition to select, targeted areas of hair. For example, brush 24 can have length L, width W and thickness T. The Width W of brush 24 can be chamfered at angle α at the distal end of the bristles such that brush 24 includes an end width E. Additionally, the distal tip of brush 24 can have a radius R. The proximal end of brush 24 can have a bottom width B, which in various examples can be less than width W such that brush 24 has an isosceles trapezoidal shape.

In examples, length L can be in the range of 20.5 mm to 22.5 mm. The thickness of baseplate 94 can be approximately 0.95 mm. In examples, width W can be in the range of 18.5 mm to 21.5 mm. In examples, thickness T can be in the range of 5.0 mm to 8.0 mm. In examples, end width E can be in the range of 10.4 mm to 13.4 mm. In examples, angle α can be approximately 50°. In examples, radius B can be in the range of 17.0 mm to 18.0 mm. The present inventors have found that a brush having the aforementioned dimensions is particularly well suited for applying hair dye to select, targeted areas of hair, such as at the roots of the hair, and such as for performing highlighting procedures.

To assemble hair dye applicator device 10, baseplate 94 can be positioned on base 42 of brush valve 28 such that aperture 96 surrounds discharge stem 44. As such, discharge stem 44 can extend into bristles 92 of brush 24. Next, the assembly of brush valve 28 and brush 24 can be coupled to brush holder 26. Specifically, bristles 92 of brush 24 can be inserted into brush socket 32 in brush holder 26. Brush valve 28 can be advanced until baseplate 94 of brush 24 engages brush ledge 34. Brush ledge 34 can form a rim for an orifice that has a smaller opening size that baseplate 94. As such, baseplate 94 cannot be pushed through brush socket 32. Additionally, brush valve 28 can be advanced until holder flange 84 engages base notch 88. Holder flange 84 and base notch 88 can lock, such as by a snap-fit or interference fit, to prevent brush valve 28 for backing out of brush holder 26. As such, the coupling of brush 24 to brush holder 26 and brush valve 28 provides a mechanical coupling that is not subject to alteration from exposure to chemicals or compositions, such as hair dyes. Thus, the combination of baseplate 94, brush ledge 34 and base notch 88 improves over designs, such as those using adhesive couplings.

Spring 18 can be positioned over nozzle body 52 (FIG. 9). Spring 18 can be made of stainless steel. Spring shoulder 56 can have a larger diameter than the inner diameter of spring 18 to facilitate retention of spring 18. Then, the assembly of brush 24, brush holder 26 and brush valve 28 can be positioned over nozzle body 52. Specifically, nozzle body 52 can be inserted into nozzle pocket 82 formed between nozzle flange 80 and slide post 46. Spring 18 can engage the free, axial end of nozzle flange 80. As such, slide post 46 of brush valve 28 can be free to slide longitudinally along nozzle body 52, with spring 18 resiliently biasing brush valve 28 away from tube head 14.

To secure brush assembly 20 with tube 12, brush holder 26 can be pushed down onto tube head 14 so that flange 38 engages flange 60 (and is positioned closer to tube 12 than flange 60) on tube head 14. Brush holder 26 can be rotated such that holder rails 62A and 62B align with rail slots 90A and 90B, respectively. Flange 60 prevents brush holder 26 from decoupling from nozzle 16 under force from spring 18. However, flange 60 is located a distance away from the region of tube head 14 including thread 54 to form a channel, and flange 38 is shorter than this distance such that brush holder 26 can traverse a longitudinal distance while slide post 46 slides along nozzle body 52. Engagement of rails 62A and 62B and slots 90A and 90B can facilitate sliding of brush holder 26 relative to tube head 14 so that coupling of cap 22 with tube head 14 can push brush holder 26 straight down onto tube head 14.

At rest, spring 18 can push brush valve 28 away from nozzle 16 such that baffle 50 is disengaged from valve seat 48. As such, liquid or composition within interior 68 of tube 12 can pass through apertures 64, between spokes 66, to enter nozzle body 52 and flow past baffle 50 and into an aperture in valve seat 48 located along passage 86. The liquid or composition can then enter discharge stem 44 and enter into bristles 92. Apertures 64 and spokes 66 can be configured to provide any number of passages through tube head 14. Spokes 66 can be configured to support baffle 50 within nozzle body 52 while permitting flow therethrough.

However, when cap 22 is assembled with tube head 14, baffle 50 can engage valve seat 48 to close-off the orifice therein, thereby preventing passage of liquid or composition surrounding baffle 50 within slide post 46 from entering discharge stem 44. Baffle 50 can be configured to engage valve seat 48 when thread 78 of cap fully engages thread 54 on tube head 14. Baffle 50 can, therefore, function as a valve stem.

Hair dye applicator device 10 can comprise part of a beauty care kit, preferably a hair coloring and/or bleaching kit. The kit can comprise the beauty care product as described hereinbefore. It also can comprise at least an additional product, alternatively from about 2 to about 4 additional products, alternatively 2 or 3 additional products. The additional products may be selected from the group consisting of a product comprising a packaged component, a tool, an instruction sheet, a protective device such as a glove, or combinations thereof. Gloves can comprise latex/natural rubber plus chemical compounds added to the liquid rubber sap during processing, nitrile gloves made of copolymer of butadiene and acrylonitrile, vinyl or polyvinyl chloride gloves, or polyethylene gloves. The packaged component may be selected from a tint component comprising at least one primary precursor, a component comprising at least a secondary precursor, a conditioning component comprising at least one conditioning active ingredient. Said components may be packaged in any suitable packaging, alternatively from a sealable container, optionally sealed with a sealable means; or a sachet. Said tool may be selected from any tool suitable for coloring and/or bleaching hair, alternatively from a comb, a spatula, a brush, a bowl for missing the components. The instruction sheet may comprise any suitable information, e.g. the step sequence, about on how to color and/or bleach hair with said kit. Any of the disclosure in relation to the first aspect is also relevant to and compatible with the second aspect.

The systems, devices and methods discussed in the present application can be useful in selectively applying semipermanent hair dye to select areas of hair. An applicator brush can be desirably sized to engage with targeted sections of hair. An applicator device can be configured so that the hair dye can be applied and reused at a later date without spoiling the hair dye. The applicator device can include a collapsible reservoir body for holding the hair dye to prevent air from being drawing into the reservoir body and interacting with the hair dye, thereby decomposing the hair dye. The applicator device can include a valve to close-off the hair dye to the atmosphere, such when coupled with a cap that can further protect the brush, and hair dye remaining therein, and prevent air from entering the reservoir body. The applicator device can be assembled using mechanical couplings that are not affected by the presence of or interaction with the hair dye. For example, a brush of the applicator device can be coupled to a valve mechanism via a mechanically interlocking connection that eliminates the need for adhesive coupling.

Various Notes

Each of these non-limiting examples can stand on its own or can be combined in various permutations or combinations with one or more of the other examples.

In this document, including in all embodiments of all aspects of the present invention, the following definitions apply unless specifically stated otherwise. All percentages are by weight of the total composition. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein "min" means "minute" or "minutes". Herein "mol" means mole. Herein "g" following a number means "gram" or "grams". All weights as they pertain to listed ingredients are based on 5 the active level and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "in at least one embodiment" means that one or more embodiments of the present invention has/have the subsequently described feature.

"Molecular weight" or "M.Wt." or "MW" and grammatical equivalents mean the number average molecular weight.

"Water-soluble" refers to any material that is sufficiently soluble in water that when dissolved forms a clear solution to the naked eye at a concentration of 0.1 g of the material in 1 Litre of deionised water at 25° C. and 1 atm pressure. The term "water-insoluble" refers to any material that is not "water-soluble".

"Substantially free from" or "substantially free of" means less than about 1%, or less than 0.8%, or less than 0.5%, or less than 0.3%, or about 0%, by total weight of the composition or formulation.

"Hair" means mammalian keratin fibres including scalp hair, facial hair and body hair. It includes such hair still being attached to a living subject and also hair that has been removed therefrom such as hair swatches and hair on a doll/mannequin. In an embodiment, "hair" means human hair. "Hair shaft" or "hair fibre" means an individual hair strand and may be used interchangeably with the term "hair."

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization.

"Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

As used herein, when describing the container according to the present invention, the expressions "bottom" and "top" are relative to the orientation of the product when resting onto a surface so that the base section of the container (also called bottom section) is orientated toward the bottom of the product and the neck section and sealing means are orientated toward the top of product. Likewise, the expressions "vertical/vertically" and "horizontal/horizontally" are relative to the orientation of the product when resting onto a surface, said surface being horizontal.

As used herein, when describing the panels forming the body section of the container, "front", "back" and "side" are relative to the panel onto which the front label is attached, said front label being the label displaying information about the product to be seen first by the consumer when standing on the supermarket shelf, including, but not limited to, the brand name, logo, slogan, illustrations and/or pictures, information such as the container size, etc.

As a used herein, "beauty care products" means any products being suitable for application onto keratin substrates, including hair, skin, eyebrows, eyelashes, lips, and nails. Beauty care products may include personal care products, make-up products, shave care products and hair care products. Personal care products may include personal and/or facial cleansing products. Make-up products may include mascaras, foundations and enamels. Hair care products may include shampoos, conditioning compositions, styling compositions and hair color compositions.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

CLAUSES

Clause 1: A method for treating hair strands, with a treatment composition contained in an applicator device, the method comprising: grasping an applicator device having a reservoir containing a temporary hair treatment composition comprised of a semi-permanent oxidative and/or direct dye hair color; applying pressure to the applicator device to force the temporary hair treatment composition out of a nozzle of the applicator device: flowing the temporary hair treatment composition from the nozzle into an applicator assembly attached to the nozzle; engaging the applicator assembly directly with a target area of the hair strands; leaving the temporary hair treatment on the target area for a time period; rinsing the temporary hair treatment composition from the hair strands; and closing the applicator device to preserve any temporary hair treatment composition remaining in the reservoir.

Clause 2: The method of clause 1, wherein the reservoir is sized to provide multiple applications of the temporary hair treatment composition to the target area in a range of one to five applications.

Clause 3: The method of clause 2, wherein the reservoir has a volumetric size of approximately fifteen milliliters to approximately seventy-five milliliters.

Clause 4: The method of clause 3, wherein the reservoir has a diameter of approximately twenty-five millimeters to approximately thirty millimeters.

Clause 5: The method of clause 1, wherein forcing temporary hair treatment composition out of the nozzle comprises passing the temporary hair treatment composition through one or more orifices.

Clause 6: The method of clause 1, wherein the applicator assembly is fluidly connected to the reservoir via an air valving system that limits inflow of air into the reservoir.

Clause 7: The method of clause 6, further comprising removing a cap from the applicator assembly of the applicator device to open the air valving system.

Clause 8: The Method of clause 7, wherein removing the cap comprises unscrewing or unsnapping the cap from the applicator assembly.

Clause 9: The method of clause 6, further comprising pushing the applicator assembly away from the nozzle via a spring to open the valving system.

Clause 10: The method of clause 1, wherein the time period comprises about five minutes to about thirty minutes Clause 11: The method of clause 1, wherein a material defining the reservoir has a permeability, sufficient to prevent $O_2$ and moisture from entering the reservoir through the material.

Clause 12: The method of clause 1, wherein the reservoir is formed by a bottle, tube pouch, sachet, tottle or an airless canister.

Clause 13: The method of clause 1, wherein applying pressure to the applicator device comprises squeezing a tube defining the reservoir, pumping the temporary hair treatment composition out of the reservoir, pouring the temporary hair treatment composition out of the reservoir or folding a tube defining the reservoir.

Clause 14: The method of clause 13 wherein applying pressure to the applicator device to force the temporary hair treatment composition out of the nozzle of the applicator comprises collapsing a tube defining the reservoir by mechanically deforming the tube.

Clause 15: The method of clause 14, wherein the tube mechanically retains a collapsed shape after pressure has been applied to the tube.

Clause 16: The method of clause 14, wherein the tube is made of a material comprising a glossy. ABL (Aluminum Barrier Layer) laminate.

Clause 17: The method of clause 1, wherein the temporary hair treatment composition has a temporary effect capable of withstanding ten or more wash cycles.

Clause 18: The method of clause 17, wherein the temporary hair treatment composition comprises a least one oxidative dye and at least one direct dye.

Clause 19: The method of clause 18, wherein the temporary hair treatment composition further comprises at least one alkalizing agent, surfactant, fatty substance, oxidizing agent or combination thereof.

Clause 20: The method of clause 1, wherein the applicator assembly comprises an applicator head selected from the group consisting of a brush, sponge, non-woven material, woven material or a comb.

Clause 21: The method of clause 20, wherein the application assembly comprises an applicator head selected from the group consisting of a detachable applicator head, a telescoping applicator head, a flexible applicator head or a hinged applicator head.

Clause 22: The method of clause 20, wherein the applicator head has a plurality of bristles having a length of 21.5 mm+/−1.5 mm, a maximum width of 20.0 mm+/−1.5 mm and a thickness of 6.5 mm+/−1-1.5 mm.

Clause 23: The method of clause 22, wherein the width of the plurality of bristles increases as the plurality of bristles extend away from the applicator device and the distal most end of the plurality of bristles is chamfered.

Clause 24: The method of clause 20 wherein the applicator head comprises one or more of the follow shapes or geometries: rounded, square, semi-circular and trapezoidal.

Clause 25: The method of clause 20, further comprising removing the applicator head and replacing the removed applicator head with another applicator head of a different size, type or material.

Clause 26: The method of clause 20, further comprising providing a plurality of applicator heads of different styles, size, shape and materials with the applicator device.

Clause 27: The method of clause 26, further comprising fluidly coupling multiple applicator heads to the reservoir at the same time.

Clause 28: The method of clause 20, wherein the applicator head comprises: a brush having a baseplate; a brush holder positioned on a first side of the base plate; and a brush valve connected to the brush holder at a second side of the baseplate.

Clause 29: A hair treatment kit comprising: a hair treatment composition selected from the group of semi-permanent oxidative and/or direct dye hair colorant compositions, hair bleaching compositions, highlighting compositions, and combinations thereof a reservoir for holding the temporary hair treatment composition; and an applicator fluidly connected to the reservoir for selectively applying the hair treatment composition to a targeted area of hair.

Clause 30: The hair treatment kit of clause 29, wherein the applicator comprises one or more applicator orifices.

Clause 31: The hair treatment kit of clause 30, wherein the one or more applicator orifices have a total orifice area of from 2-10 mm.

Clause 32: The hair treatment kit of clause 30, wherein the applicator comprises a brush, sponge, non-woven material, woven material or a comb.

Clause 33: The hair treatment kit of clause 30, wherein the applicator is detachably couplable to the reservoir.

Clause 34: The hair treatment kit of clause 30, further comprising multiple applicators of different sizes, shapes or styles.

Clause 35: The hair treatment kit of clause 30, wherein the applicator has a plurality of bristles having a length of 21.5 mm+/−1.5 mm, a maximum width of 20.0 mm+/−1.5 mm and a thickness of 6.5 mm+/−1.5 mm.

Clause 36: The hair treatment kit of clause 30, further comprising a valve assembly connecting the reservoir to the applicator.

Clause 37: The hair treatment kit of clause 36, further comprising an applicator locking device coupling the applicator to the valve assembly.

Clause 38: The hair treatment kit of clause 30, further comprising a set of instructions directing a user to dispense the temporary hair treatment composition directly from the reservoir dispenser onto target hair roots and hairline.

Clause 39: The hair treatment kit of clause 30, wherein the temporary hair treatment composition comprises at least one oxidative dye and at least one direct dye.

Clause 40: The hair treatment kit of clause 30, wherein the reservoir is fabricated a glossy ABL (Aluminum Barrier Layer) laminate.

Clause 41: The hair treatment kit of clause 30, further comprising multiple reservoir packages.

Clause 42: The hair treatment kit of clause 41, wherein the multiple reservoir packages each contain an identical temporary hair treatment composition.

Clause 43: The hair treatment kit of clause 41, wherein the multiple reservoir packages each contain a different temporary hair treatment composition.

Clause 44: An applicator device for applying a semi-permanent oxidative and/or direct dye hair colorant composition to a selected area of hair, the applicator device comprising: a collapsible body defining a reservoir for holding the hair colorant composition; a body head connected to the collapsible body and defining a nozzle in fluid communication with the reservoir; an applicator assembly connected to the body head, the applicator assembly comprising a valve body configured to engage the nozzle to selectively permit flow from the reservoir, an applicator mechanically attached to the valve body to receive flow from the valve body, and a holder having an opening through which a portion of the applicator can extend, the holder coupled to the body head; and a spring located between the body head and the valve body to bias the applicator assembly away from the body head.

Clause 45: The applicator device of clause 44, wherein the nozzle defines from one to one-hundred orifices.

Clause 46: The applicator device of clause 45, wherein each orifice has a diameter of two to twenty-five millimeters.

Clause 47: The applicator device of clause 44, wherein the applicator comprises: a baseplate including an aperture; and a brush extending from a first side of the baseplate.

Clause 48: The applicator device of clause 47 wherein the valve body comprises: a base; a discharge stem extending from a first side of the base and extending through the aperture and into the brush; a slide post extending from a second side of the base and coupling with the nozzle; and a valve seat positioned between the discharge stem and the slide post.

Clause 49: The applicator device of clause 48, wherein the holder comprises: a holder body defining an opening for receiving the brush; an inner ledge for engaging the baseplate; a base notch for receiving the base; a pair of slide slots; a cap ledge located on exterior of the holder body; and a flange for engaging the body head.

Clause 50: The applicator device of clause 49, wherein the body head comprises: a main body; a channel for receiving the flange of the holder; a pair of slide rails for sliding in the pair of slide slots; a baffle located inside the nozzle to engage the valve seat; and threading for engaging a cap.

Clause 51: The applicator device of clause 50, further comprising the cap, the cap comprising: an end wall; a side wall extending from the end wall at a first end; threading located at a second end of the side wall; and an actuator ledge configured to engage the cap ledge to compress the spring when the threading engages the threading of the body head.

Clause 52: The applicator device of clause 47, wherein the brush comprises a plurality of bristles shaped to have: a length of approximately 21.5 millimeters; a thickness of approximately 6.5 millimeters; and a width of approximately twenty millimeters.

Clause 53: The applicator device of clause 52 wherein distal edges of the plurality of bristles are chamfered.

The claimed invention is:

1. A method for treating hair strands, with a treatment composition contained in an applicator device, the method comprising:
   grasping an applicator device having a reservoir containing a temporary hair treatment composition comprised of a semi-permanent oxidative and/or direct dye hair color;

applying pressure to the applicator device to force the temporary hair treatment composition out of a nozzle of the applicator device;

removing a cap from an applicator assembly attached to the nozzle to open an air valving system that limits inflow of air into the reservoir, wherein the applicator assembly is fluidly connected to the reservoir via the air valving system;

flowing the temporary hair treatment composition from the nozzle into the applicator assembly;

engaging the applicator assembly directly with a target area of the hair strands;

leaving the temporary hair treatment on the target area for a time period;

rinsing the temporary hair treatment composition from the hair strands; and closing the applicator device to preserve any temporary hair treatment composition remaining in the reservoir.

2. The method of claim 1, wherein forcing temporary hair treatment composition out of the nozzle comprises passing the temporary hair treatment composition through one or more orifices.

3. The method of claim 1, wherein removing the cap comprises unscrewing or unsnapping the cap from the applicator assembly.

4. The method of claim 1, further comprising pushing the applicator assembly away from the nozzle via a spring to open the valving system.

5. The method of claim 1, wherein applying pressure to the applicator device comprises squeezing a tube defining the reservoir, pumping the temporary hair treatment composition out of the reservoir, pouring the temporary hair treatment composition out of the reservoir or folding a tube defining the reservoir.

6. The method of claim 1, wherein the applicator assembly comprises an applicator head selected from the group consisting of a brush, sponge, non-woven material, woven material or a comb.

7. The method of claim 6, wherein the applicator assembly comprises an applicator head selected from the group consisting of a detachable applicator head, a telescoping applicator head, a flexible applicator head or a hinged applicator head.

8. The method of claim 6, wherein the applicator head comprises:
a brush having a baseplate;
a brush holder positioned on a first side of the base plate; and
a brush valve connected to the brush holder at a second side of the baseplate.

9. A hair treatment kit comprising:
a hair treatment composition selected from the group of semi-permanent oxidative and/or direct dye hair colorant compositions, hair bleaching compositions, highlighting compositions, and combinations thereof;
a reservoir for holding the temporary hair treatment composition; and
an applicator fluidly connected to the reservoir via an air valving system that limits inflow of air into the reservoir for selectively applying the hair treatment composition to a targeted area of hair, where the applicator includes a cap that is removed to open the air valving system.

10. The hair treatment kit of claim 9, wherein the applicator comprises one or more applicator orifices.

11. The hair treatment kit of claim 10, wherein the applicator is detachably couplable to the reservoir.

12. The hair treatment kit of claim 10, further comprising a valve assembly connecting the reservoir to the applicator.

13. The hair treatment kit of claim 12, further comprising an applicator locking device coupling the applicator to the valve assembly.

14. The hair treatment kit of claim 10, further comprising multiple reservoir packages.

15. An applicator device for applying a semi-permanent oxidative and/or direct dye hair colorant composition to a selected area of hair, the applicator device comprising:
a collapsible body defining a reservoir for holding the hair colorant composition;
a body head connected to the collapsible body and defining a nozzle in fluid communication with the reservoir;
an applicator assembly connected to the body head, the applicator assembly comprising:
a valve body configured to engage the nozzle to selectively permit flow from the reservoir;
an applicator mechanically attached to the valve body to receive flow from the valve body; and
a holder having an opening through which a portion of the applicator can extend, the holder coupled to the body head; and
a spring located between the body head and the valve body to bias the applicator assembly away from the body head.

16. The applicator device of claim 15, wherein the applicator comprises:
a baseplate including an aperture; and
a brush extending from a first side of the baseplate.

17. The applicator device of claim 16, wherein the valve body comprises:
a base;
a discharge stem extending from a first side of the base and extending through the aperture and into the brush;
a slide post extending from a second side of the base and coupling with the nozzle; and
a valve seat positioned between the discharge stem and the slide post.

18. The applicator device of claim 17, wherein the holder comprises:
a holder body defining an opening for receiving the brush;
an inner ledge for engaging the baseplate;
a base notch for receiving the base;
a pair of slide slots;
a cap ledge located on exterior of the holder body; and
a flange for engaging the body head.

\* \* \* \* \*